United States Patent [19]

Hirai et al.

[11] Patent Number: 4,476,133
[45] Date of Patent: * Oct. 9, 1984

[54] TRIAZOLO-4,1-BENZOXAZEPINES HAVING CNS ACTIVITY

[75] Inventors: Kentaro Hirai, Kyoto; Shigeru Matsutani, Osaka; Itsuo Makino, Hyogo; Teruyuki Ishiba, Osaka, all of Japan

[73] Assignee: Shionogi & Co., Ltd., Osaka, Japan

[ * ] Notice: The portion of the term of this patent subsequent to Oct. 27, 1998 has been disclaimed.

[21] Appl. No.: 397,855

[22] Filed: Jul. 13, 1982

Related U.S. Application Data

[62] Division of Ser. No. 250,299, Apr. 2, 1981, Pat. No. 4,324,842.

[30] Foreign Application Priority Data

Apr. 18, 1980 [JP] Japan ................................. 55-52185
Sep. 29, 1980 [JP] Japan ................................. 55-136646

[51] Int. Cl.³ .................... A61K 31/55; C07D 498/04
[52] U.S. Cl. .................................. 424/269; 260/245.5
[58] Field of Search ...................... 260/245.5; 424/269

[56] References Cited

U.S. PATENT DOCUMENTS 3,681,343  8/1972  Hester .............................. 260/245.5
4,297,280  10/1981  Hirai et al. ....................... 260/245.5

FOREIGN PATENT DOCUMENTS 2947773  6/1980  Fed. Rep. of Germany .
55-72177  5/1980  Japan .
2046729  11/1980  United Kingdom .

OTHER PUBLICATIONS

Hirai et al., Chem. Abstracts, vol. 93, Abstract No. 204705p (1980).

Primary Examiner—Alton D. Rollins
Attorney, Agent, or Firm—Wenderoth, Lind & Ponack

[57] ABSTRACT 4,1-Benzoxazepines of the following formula are novel central nervous system:

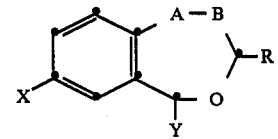

wherein
R is hydrogen or $C_1$ to $C_5$ alkyl;
X is hydrogen, halogen, or nitro;
Y is phenyl, 2-halophenyl, 4-halophenyl, 2-trifluoromethylphenyl, or pyridyl;
and

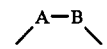

is a group of the formula:

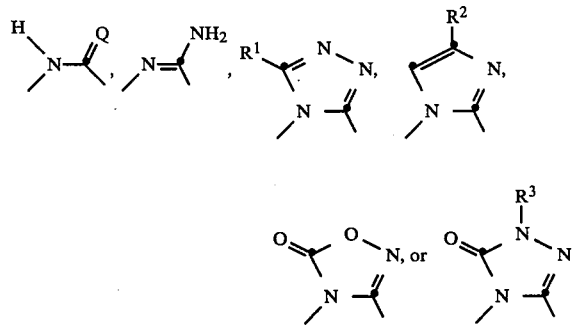

(wherein Q is oxygen, sulfur, or hydrazono, with a proviso that, when Y is phenyl or 2-halophenyl and R is hydrogen, Q is neither oxygen nor sulfur;
$R^1$ is hydrogen, halogen, $C_1$ to $C_5$ alkyl, $C_1$ to $C_5$ alkylthio, 5- or 6-membered heterocycle or $C_1$ to $C_5$ alkyl substituted by a substituent selected from the group consisting of halogen, hydroxy, mercapto, $C_1$ to $C_5$ alkoxy, $C_1$ to $C_5$ alkanoyloxy, $C_1$ to $C_5$ alkylthio, $C_7$ to $C_9$ aralkyldithio, $C_2$ to $C_{10}$ dialkylamino, $C_3$ to $C_{15}$ dialkylaminoalkoxy, $C_3$ to $C_{15}$ dialkylaminoalkylthio, and 5- or 6-membered heterocycle;
$R^2$ is $C_1$ to $C_5$ alkyl;
and $R^3$ is $C_1$ to $C_5$ alkyl or $C_3$ to $C_{10}$ dialkylaminoalkyl;
with a proviso that when $R^1$ is $C_1$ to $C_5$ alkyl and R is hydrogen, Y is neither phenyl nor 2-halophenyl)

6 Claims, No Drawings

TRIAZOLO-4,1-BENZOXAZEPINES HAVING CNS ACTIVITY

This application is a division of application Ser. No. 250,299, filed Apr. 2, 1981 (now U.S. Pat. No. 4,374,842).

BACKGROUND OF THE INVENTION

Various 1,4-benzodiazepine compounds including nitrazepam, diazepam, medazepam, estazolam, and triazolam have been used practically as hypnotics, minor tranquilizers, or psychotropic agents. Recently, metal disorders have shown a tendency to rapidly increase as the human society is complicated. The present inventors have investigated to develop drugs acting on the central nervous system (hereinafter abbreviated as "CNS") more effectively and which are broadly applicable to mental disorders, and have succeeded in developing novel CNS drugs, (U.S. see our copending patent application Ser. No. 91,814 filed Nov. 6, 1979 (now U.S. Pat. No. 4,297,280). The present invention provides a novel type of CNS drugs, i.e. 4,1-benzoxazepines having potent central nervous system actions. The compounds having 1,4-benzodiazepine structure are known to show a variety of CNS actions, but 4,1-benzoxazepine derivatives are not so generally active as CNS drugs. Some 4,1-benzoxazepine derivatives have been described in German Pat. No. 1,545,639, U.S. Pat. No. 3,346,638, Farmaco. Ed. Sci., 18, 815 (1963) and Ann. Chem., 1978, 1241. The compounds of this invention shown hereinafter are novel and quite different from the above-cited known 4,1-benzoxazepine derivatives in potency and diversity of the CNS actions and in chemical structure.

SUMMARY OF THE INVENTION

This invention relates to novel 4,1-benzoxazepines having potent CNS actions.

The compounds of this invention are represented by the general formula (I):

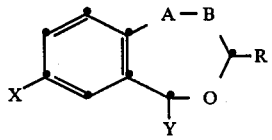

[wherein
R is hydrogen or $C_1$ to $C_5$ alkyl;
X is hydrogen, halogen, or nitro;
Y is phenyl, 2-halophenyl, 4-halophenyl, 2-trifluoromethylphenyl, or pyridyl; and

is a group of the formula:

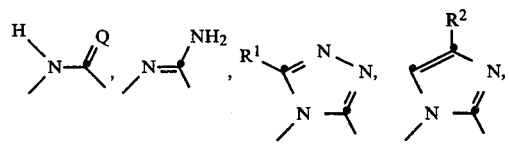

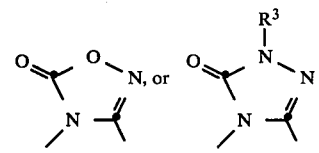

(wherein
Q is oxygen, sulfur, or hydrazono, with a proviso that, when Y is phenyl or 2-halophenyl and R is hydrogen, Q is neither oxygen nor sulfur;
$R^1$ is hydrogen, halogen, $C_1$ to $C_5$ alkyl, $C_1$ to $C_5$ alkylthio, 5- or 6-membered heterocycle or $C_1$ to $C_5$ alkyl substituted by a substituent selected from the group consisting of halogen, hydroxy, mercapto, $C_1$ to $C_5$ alkoxy, $C_1$ to $C_5$ alkanoyloxy, $C_1$ to $C_5$ alkylthio, $C_7$ to $C_9$ aralkyldithio, $C_2$ to $C_{10}$ dialkylamino, $C_3$ to $C_{15}$ dialkylaminoalkylthio, and 5- or 6-membered heterocycle;
$R^2$ is $C_1$ to $C_5$ alkyl; and
$R^3$ is $C_1$ to $C_5$ alkyl or $C_3$ to $C_{10}$ dialkylaminoalkyl;
with a proviso that when $R^1$ is $C_1$ to $C_5$ alkyl and R is hydrogen, Y is neither phenyl nor 2-halophenyl)]

DETAILED EXPLANATION

Compounds (I) of this invention may also be the acid addition salts, particularly non-toxic pharmaceutically acceptable salts, for example, salts with inorganic acids such as hydrochloric acid, hydrobromic acid, hydroiodic acid, sulfuric acid, phosphoric acid, nitric acid, etc. and salts with organic acids such as acetic acid, oxalic acid, succinic acid, phthalic acid, malic acid, tartaric acid, maleic acid, citric acid, mandelic acid, ascorbic acid, methanesulfonic acid, toluenesulfonic acid etc.

In the aforementioned definition, $C_1$ to $C_5$ alkyl means a straight or branched $C_1$ to $C_5$ alkyl, e.g. methyl, ethyl, propyl, isopropyl, butyl, isobutyl, sec-butyl, t-butyl, pentyl, etc. Halogen means fluorine, chlorine, and bromine. $C_1$ to $C_5$ Alkylthio includes methylthio, ethylthio, propylthio, isopropylthio, butylthio, isobutylthio, s-butylthio, t-butylthio, pentylthio, and the like. 5- or 6-Membered heterocycle means saturated or unsaturated 5- or 6-membered heterocycle containing 1 to 2 hetero atoms such as nitrogen atom, oxygen atom, and/or sulfur atom e.g. pyrrolidinyl, oxazolidino, thiazolidinyl, imidazolidinyl, pyrazolidinyl, piperidino, piperazinyl, morpholino, etc. $C_1$ to $C_5$ Alkoxy includes methoxy, ethoxy, propoxy, isopropoxy, butoxy, isobutoxy, sec-butoxy, t-butoxy, pentyloxy, etc. $C_1$ to $C_5$ Alkanoyloxy includes formyloxy, acetoxy, propionyloxy, butyryloxy, isobutyryloxy, valeryloxy, isovaleryloxy, etc. $C_7$ to $C_9$ Aralkyldithio includes benzyldithio, phenethyldithio, tolylethyldithio, etc. $C_2$ to $C_{10}$ Dialkylamino means symmetrical dialkylamino such as dimethylamino, diethylamino, dipropylamino, dibutylamino, dipentylamino, etc and asymmetrical dialkylamino such as methylethylamino, methylpropylamino, ethylpropylamino, etc. $C_3$ to $C_{15}$ Dialkylaminoalkoxy means the above $C_1$ to $C_5$ alkoxy substituted by the above $C_2$ to $C_{10}$ dialkylamino. $C_3$ to $C_{15}$ Dialkylaminoalkylthio means the above $C_1$ to $C_5$ alkylthio substituted by the above $C_1$ to $C_5$ dialkylamino.

Representative of Compounds [I] are as follows:
(1) 2-oxo-5-(trifluoromethylphenyl)-1,2,3,5-tetrahydro[4,1]-benzoxazepine (2) 2-oxo-5-(2-trifluoromethylphenyl)-7-chloro-1,2,3,5-tetrahydro[4,1]benzoxazepine
(3) 2-oxo-5-(2-pyridyl)-7-chloro-1,2,3,5-tetrahydro[4,1]-benzoxazepine
(4) 2-oxo-3-methyl-5-(2-chlorophenyl)-7-chloro-1,2,3,5-tetrahydro[4,1]benzoxazepine
(5) 2-oxo-5-phenyl-1,2,3,5-tetrahydro[4,1]benzoxazepine
(6) 2-oxo-5-(4-chlorophenyl)-1,2,3,5-tetrahydro[4,1-]benzoxazepine
(7) 2-thioxo-5-(2-trifluoromethylphenyl)-1,2,3,5-tetrahydro[4.1]-benzoxazepine
(8) 2-amino-5-(2-chlorophenyl)-7-chloro-3,5-dihydro[4,1]-benzoxazepine
(9) 6-(2-chlorophenyl)-8-chloro-4H,6H-(1,2,4)triazolo[4,3-a]-[4,1]benzoxazepine
(10) 6-phenyl-8-chloro-4H,6H-(1,2,4)triazolo[4,3-a][4,1]-benzoxazepine
(11) 6-(2-pyridyl)-8-chloro-4H,6H-(1,2,4)triazolo[4,3-a][4,1]-benzoxazepine
(12) 1-bromo-6-(2-chlorophenyl)-8-chloro-4H,6H-(1,2,4)triazolo[4,3-a][4,1]benzoxazepine
(13) 1-methyl-6-(2-trifluoromethylphenyl)-4H,6H-(1,2,4)triazolo[4,3-a][4,1]benzoxazepine
(14) 1,4-dimethyl-6-(2-chlorophenyl)-4H,6H-(1,2,4)triazolo[4,3-a][4,1]benzoxazepine
(15) 1-methylthio-6-(2-chlorophenyl)-8-chloro-4H,6H-(1,2,4)triazolo[4,3-a][4,1]benzoxazepine
(16) 1-chloromethyl-6-(2-chlorophenyl)-8-chloro-4H,6H-(1,2,4)triazolo[4,3-a][4,1]benzoxazepine
(17) 1-chloromethyl-4-methyl-6-(2-chlorophenyl)-8-chloro-4H,6H-(1,2,4)triazolo[4,3-a][4,1]benzoxazepine
(18) 1-(4-methylpiperazino)-6-(2-chlorophenyl)-8-chloro-4H,6H-(1,2,4)triazolo[4,3-a][4,1]benzoxazepine
(19) 1-morpholino-6-phenyl-8-chloro-4H,6H-(1,2,4)triazolo[4,3-a][4,1]benzoxazepine
(20) 1-mercaptomethyl-6-(2-chlorophenyl)-8-chloro-4H,6H-(1,2,4)triazolo[4,3-a][4,1]benzoxazepine
(21) 1-methoxymethyl-6-(2-chlorophenyl)-8-chloro-4H,6H-(1,2,4)triazolo[4,3-a][4,1]benzoxazepine
(22) 1-acetoxymethyl-6-(2-chlorophenyl)-8-chloro-4H,6H-(1,2,4)triazolo[4,3-a][4,1]benzoxazepine
(23) 1-hydroxymethyl-6-(2-chlorophenyl)-8-chloro-4H,6H-(1,2,4)triazolo[4,3-a][4,1]benzoxazepine
(24) 1-methylthiomethyl-6-(2-chlorophenyl)-8-chloro-4H,6H-(1,2,4)triazolo[4,3-a][4,1]benzoxazepine
(25) 1-benzyldithiomethyl-6-(2-chlorophenyl)-8-chloro-4H,6H-(1,2,4)triazolo[4,3-a][4,1]benzoxazepine
(26) 1-(N,N-dimethylamino)methyl-6-(2-chlorophenyl)-8-chloro-4H,6H-(1,2,4)triazolo[4,3-a][4,1]benzoxazepine
(27) 1-(1-pyrrolidinyl)methyl-6-(2-chlorophenyl)-8-chloro-4H,6H-(1,2,4)triazolo[4,3-a][4,1]benzoxazepine
(28) 1-[2-(N,N-dimethylamino)ethyl]-6-(2-chlorophenyl)-8-chloro-4H,6H-(1,2,4)triazolo[4,3-a][4,1]benzoxazepine
(29) 1-(N,N-dimethylaminopropyl)-6-(2-chlorophenyl)-8-chloro-4H,6H-(1,2,4)triazolo[4,3-a][4,1]benzoxazepine
(30) 1-[2-(N,N-dimethylamino)ethyloxymethyl]-6-(2-chlorophenyl)-8-chloro-4H,6H-(1,2,4)triazolo[4,3-a][4,1]benzoxazepine
(31) 2-methyl-6-(2-chlorophenyl)-8-chloro-4H,6H-imidazo[1,2-a][4,1]benzoxazepine
(32) 1-oxo-6-(2-chlorophenyl)-8-chloro-1H,4H,6H-(1,2,4)oxadiazolo[4,3-a][4,1]benzoxazepine
(33) 1-oxo-2-methyl-6-(2-chlorophenyl)-8-chloro-1,2-dihydro-4H,6H-(1,2,4)triazolo[4,3-a][4,1]benzoxazepine
(34) 1-oxo-2-[2-(N,N-dimethylamino)ethyl]-6-(2-chlorophenyl)-8-chloro-1,2-dihydro-4H,6H-(1,2,4)triazolo[4,3-a][4,1]benzoxazepine Preparations The preparation of Compound (I) varies with the species of substituents as follows:

(1) In cases that

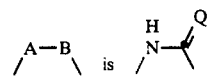

Reaction Scheme A

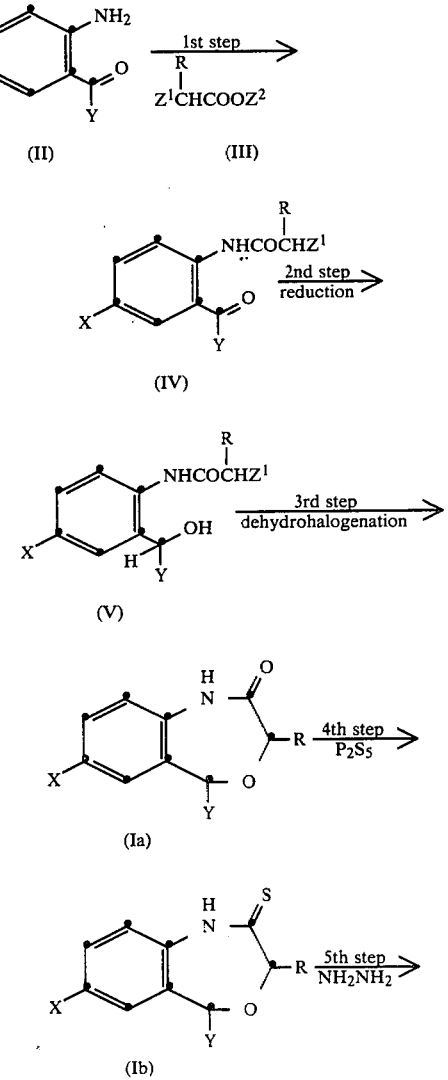

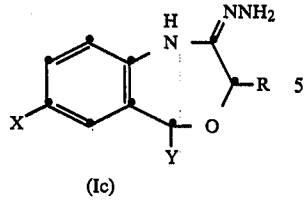

(Ic)

(wherein R, X, and Y are the same as mentioned above; $Z^1$ and $Z^2$ each is halogen)

(First step)

The first step, the reaction of the starting materials (II) with the halogenoacetyl halogenides (III), is achieved in a conventional manner for the amide formation. Representatives of halogenoacetyl halogenides (III) are chloroacetyl chloride, bromoacetyl bromide, and the like. This reaction is preferably effected in a suitable solvent (e.g. methanol, ethanol, isopropanol, ethylene glycol, benzene, pyridine, and the like) under heating at a temperature around the boiling point of the solvent used. It is preferred to employ an equal or excess amount of the halogenoacetyl halogenide (III) to 1 mole of the starting compound (II). The reaction may be accelerated by addition of a suitable base such as triethylamine, quinoline, pyridine, and the like. The starting materials (II) have been described in Journal of Organic Chemistry 26, 4488 (1961) and Journal Pharmaceutical Science 53, 264 (1964).

(Second step)

The second step, the reduction of the aryl carbonyl group of the compounds (IV), can readily be achieved in a conventional manner. The reduction may be carried out with a reducing agent in a suitable inert solvent under cooling below room temperature. Representatives of the reducing agents are metal hydrides such as sodium borohydride, lithium borohydride, diborane, and the like. Representatives of the inert solvents are dimethylformamide, hexamethylphosphoric triamide, and the like.

(Third step)

The third step, the dehydrohalogenation, can readily be carried out in the presence of a base in a suitable solvent at the refluxing temperature under heating. Representatives of the bases are alkali metal hydroxides, alkaline earth metal hydroxides, alkali metal alcoholates, and the like. Representatives of the solvents are ethanol, isopropanol, dioxane, benzene, and the like.

(Fourth step)

The fourth step, the reaction of the compounds (Ia) with phosphorus pentasulfide, is carried out in the presence of a base in a suitable solvent at about 30° to 120° C., preferably about 50° C. The base is employed as an accelerator. Representatives of the bases are alkali metal carbonates, alkali metal hydrogencarbonates and the like. Representatives of the solvents are dichloromethane, tetrahydrofuran, diglyme, dioxane, hexamethylphosphoric triamide, dimethylsulfoxide, and the like.

(Fifth step)

The fifth step, the reaction of the compounds (Ib) with hydrazine, is carried out in a conventional manner for amidrazone formation. The reaction is effected in a suitable solvent under cooling or at room temperature. Rpresentatives of the solvents are ethanol, chloroform, dimethylformamide, and the like.

(2) In cases that

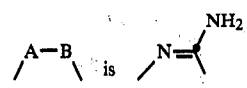

Reaction Scheme B

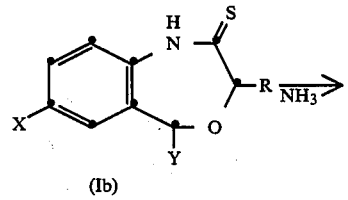

(Ib)

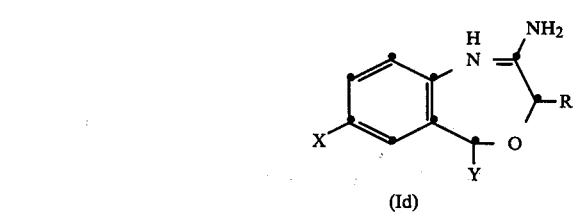

(Id)

(wherein R, X, and Y are the same as mentioned above)

The 2-amino-4,1-benzoxazepine derivatives (Id) are prepared by reacting the compounds (Ib) with an ammonia-alcohol solution. The reaction proceeds well even at room temperature and ordinarily completes within a period of several hours.

(3) In cases that

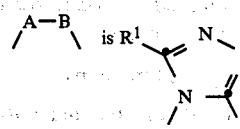

(a) In cases that $R^1$ is hydrogen, halogen, or 5- or 6-membered heterocycle

Reaction Scheme C

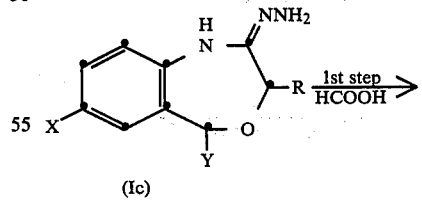

(Ic)

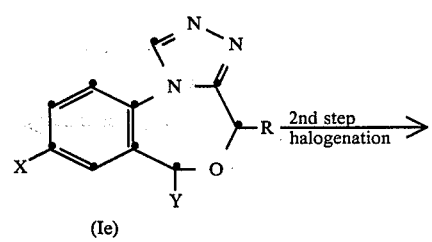

(Ie)

-continued
Reaction Scheme C

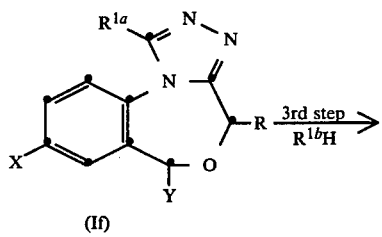

(If)

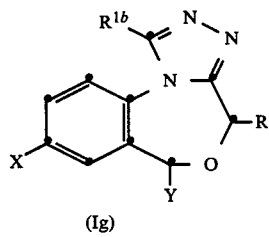

(Ig)

(wherein
X, Y, and R are the same as mentioned above;
$R^{1a}$ is halogen; and
$R^{1b}$ is 5- or 6-membered heterocycle)

(First step)

The triazolo compounds (Ie) can be prepared by reacting the compounds (Ic) with formic acid.

(Second step)

The halogenation of the compounds (Ie) to the compounds (If) is achieved with a halogenating agent in a solvent such as carbon tetrachloride, preferably under refluxing. Representatives of the halogenating agents are N-bromosuccinimide, N-chlorosuccinimide, N-bromoacetamide, and the like.

(Third step)

The compounds (If) are reacted with 5- or 6-membered heterocyclic compounds such as pyrrolidine, morpholine, N-methylpiperazine, etc to yield the compounds (Ig). The reaction is effected under heating, preferably at about 100° C.

(b) In cases that $R^1$ is $C_1$ to $C_5$ alkyl

Reaction Scheme D

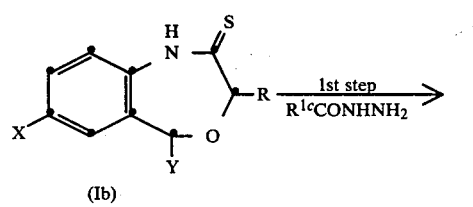

(Ib)

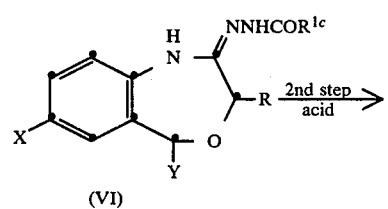

(VI)

-continued
Reaction Scheme D

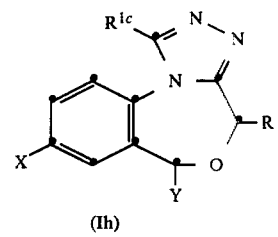

(Ih)

(wherein R, X, and Y are the same as mentioned above; and $R^{1c}$ is $C_1$ to $C_5$ alkyl)

(First step)

The first step, the preparation of the compounds (VI), is carried out by reacting the compounds (Ib) with an alkanoylhydrazine of the formula $R^{1c}CONHNH_2$. The reaction is effected in the same manner as in the 5th step of Reaction Scheme A.

(Second step)

The second step, the preparation of the compounds (Ih), is carried out by treating the compounds (VI) with an acid. The preferred acids are formic acid and acetic acid. The reaction is effected in the same manner as in the 1st step of Reaction Scheme C.

(c) In cases that $R^1$ is $C_1$ to $C_5$ alkylthio

Reaction Scheme E

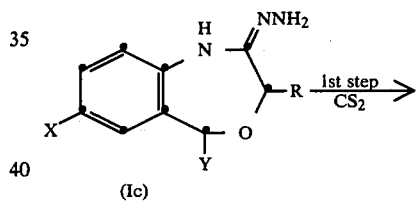

(Ic)

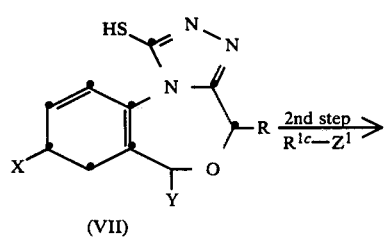

(VII)

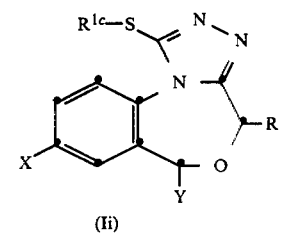

(Ii)

(wherein R, $R^{1c}$, X, Y and Z are the same as mentioned above)

(First step)

The first step, the formation of triazolo compounds (VII), is carried out by reacting the compounds (Ic) with carbon disulfide in the presence of a condensing agent such as sodium hydride, imidazole, and 2-chloro-3-methyl-4-phenylthiazolium fluorosulfonate. The reaction is effected in an inert solvent at a temperature of −30° C. to 0° C. Representatives of the inert solvents are tetrahydrofuran, tetrahydropyran, diglyme, dimethylsulfoxide, and the like.

(Second step)

The second step, the preparation of the compounds (Ii), is carried out by reacting the compounds (VII) with an alkyl halide of the formula $R^{1c}$—$Z^1$ in the presence of a base. Representatives of the bases are sodium hydride, sodium amide, sodium ethoxide, and the like. The reaction is carried out in an inert solvent under ice-cooling or at room temperature or under heating around the boiling point of the solvent. Representatives of the inert solvents are ethanol, tetrahydrofuran, dimethylformamide, dimethylsulfoxide, toluene, and the like. In cases that the alkyl halide is less reactive, an iodide compound such as sodium iodide or potassium iodide may be added in order to enhance the reactivity.

(d) In cases that $R^1$ is $C_1$ to $C_5$ alkyl substituted by halogen, $C_1$ to $C_5$ alkoxy, $C_1$ to $C_5$ alkanoyloxy, or hydroxy Reaction Scheme F

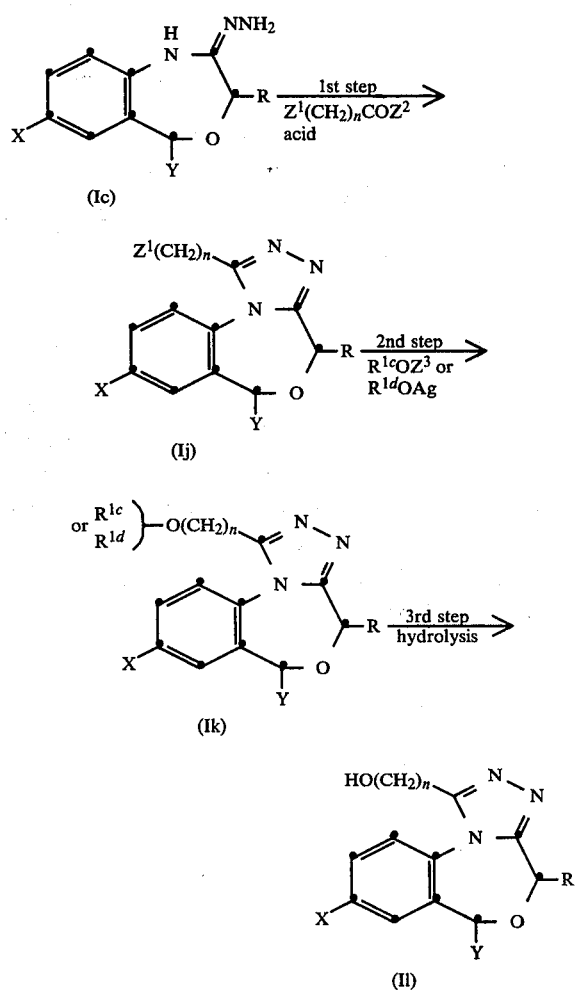

(wherein

R, $R^{1c}$, X, Y, $Z^1$, and $Z^2$ are the same as mentioned above;

n is an integer of 1 to 5;

$R^{1d}$ is $C_1$ to $C_5$ alkanoyl; and $Z^3$ is alkali metal)

(First step)

The first step, the preparation of the triazolo compounds (Ij), is carried out by reacting the compounds (Ic) with halogenoalkanoyl halogenides of the formula $Z^1(CH_2)_nCOZ^2$ in the presence of an acid. Representatives of the halogenoalkanoyl halogenides are chloroacetyl chloride, bromoacetyl bromide, chloropropionyl chloride, bromopropionyl bromide, and the like. Representatives of the acids are acetic acid, propionic acid, benzoic acid, and the like. The reaction is preferably effected at the refluxing temperature of the solvent used under heating.

(Second step)

The second step, the formation of the compounds (Ik), is carried out by reacting the compounds (Ij) with an alkali metal alcoholate of the formula $R^{1c}OZ^3$ or silver carboxylate of the formula $R^{1d}OAg$. The reaction proceeds sufficiently at room temperature, but if required, the reaction may be accelerated by heating.

(Third step)

The third step, the hydrolysis of the compounds (Ik) to the compounds (Il), is carried out by addition of an acid or alkali. Representatives of the acid are mineral acids such as hydrochloric acid, sulfuric acid, and the like, and the alkali includes alkali metal hydroxides, alkaline earth metal hydroxides, and the like.

(e) In cases that $R^1$ is $C_1$ to $C_5$ alkyl substituted by a 5- or 6-membered heterocycle Reaction Scheme G

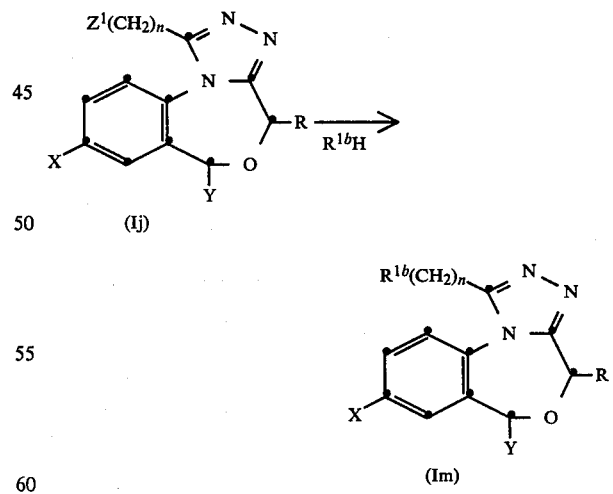

(wherein n, R, $R^{1b}$, X, Y, and $Z^1$ are the same as mentioned above)

The reaction of the compounds (Ij) with the heterocyclic compounds $R^{1b}H$ is effected in the same manner as in the 3rd step of Reaction Scheme C.

(f) In cases that $R^1$ is $C_1$ to $C_5$ alkyl substituted by mercapto or $C_7$ to $C_9$ aralkyldithio

Reaction Scheme H

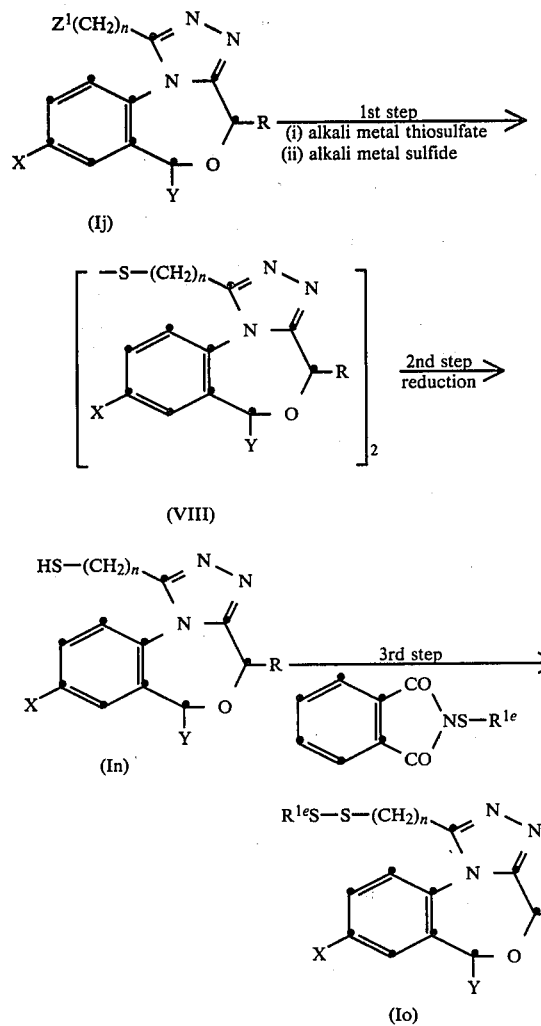

(wherein R, X, Y, $Z^1$, and n are the same as mentioned above; and $R^{1e}$ is $C_7$ to $C_9$ aralkyl)

(First step)

The compounds (Ij) are reacted with an alkali metal thiosulfate to give the corresponding alkali thiosulfate esters (Bunte's salt), and the latter are treated with an alkali metal sulfide to give the corresponding disulfides (VIII). Preferable alkali metal thiosulfates are sodium thiosulfate and potassium thiosulfate; sodium thiosulfate is most preferable. Representatives of the alkali metal sulfides are alkali metal arylsulfides (e.g. sodium phenylsulfide), alkali metal aralkylsulfides (e.g. sodium benzylsulfide), alkali metal salts of thiol type of thiamine (e.g. sodium salt, potassium salt), and the like. Among these salts, it is preferred to employ the thiol type of thiamine sodium salt.

(Second step)

The second step, the reduction of the compounds (VIII) to the compounds (In), is achieved with a reducing agent. Representatives of the reducing agents are L-cysteine, dithiothreitol, 2-mercaptoethanol, thioglycolic acid, and other reducing agents which can convert a disulfide to a thiol. The reaction is effected in an inert solvent at room temperature. Representatives of the inert solvents are methanol, ethanol, methylene chloride, chloroform, dimethylformamide, and the like.

(Third step)

The third step, the dithioester formation (formation of the compounds (Io)), is carried out by reacting the compounds (In) with an N-aralkylthiophthalimide. The reaction may be conducted at room temperature or more preferably at the refluxing temperature of the solvent under heating.

(g) In cases that $R^1$ is $C_1$ to $C_5$ alkyl substituted by $C_1$ to $C_5$ alkylthio

Reaction Scheme I

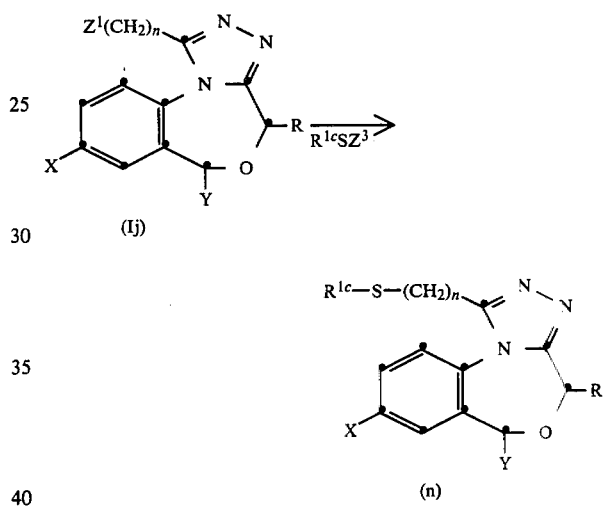

(wherein R, $R^{1c}$, X, Y, $Z^1$, $Z^3$, and n are the same as mentioned above)

The compounds of the formula (In) may be prepared by reacting the compounds (Ij) (prepared in the manner as described in Reaction Scheme F) with alkali metal sulfides of the formula $R^{1c}SZ^3$. The reaction is preferably effected under cooling or at room temperature.

(h) In cases that $R^1$ is $C_1$ to $C_5$ alkyl substituted by $C_2$ to $C_{10}$ dialkylamino

Reaction Scheme J

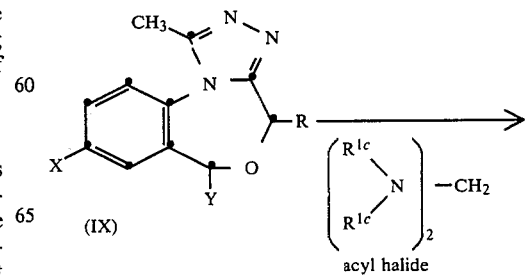

acyl halide

-continued
Reaction Scheme J

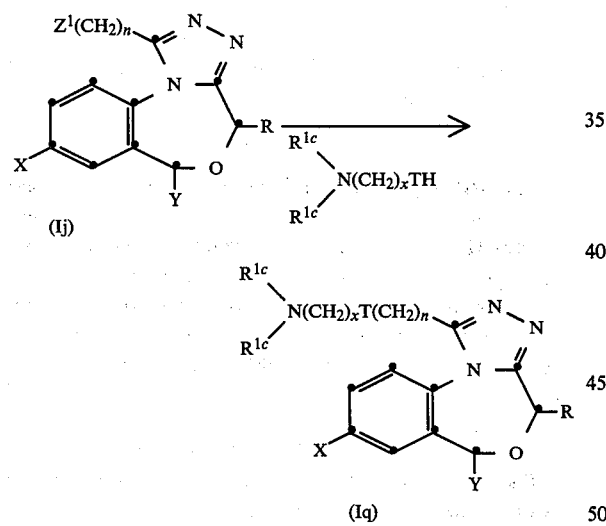

(Ip)

(wherein R, $R^{1c}$, X and Y are the same as mentioned above)

The objective compounds (Ip) are prepared by reacting the compounds of the formula (IX) with a bis(dialkylamino)alkane of the formula as mentioned in the Scheme J in the presence of an acyl halide. The starting compounds (IX) have been described in U.S. patent application No. 91,814. Representatives of the acyl halides are acetyl chloride, acetyl bromide, propionyl chloride, and the like.

(i) In cases that $R^1$ is $C_1$ to $C_5$ alkyl substituted by $C_3$ to $C_{15}$ dialkylaminoalkoxy or $C_3$ to $C_{15}$ dialkylaminoalkylthio Reaction Scheme K

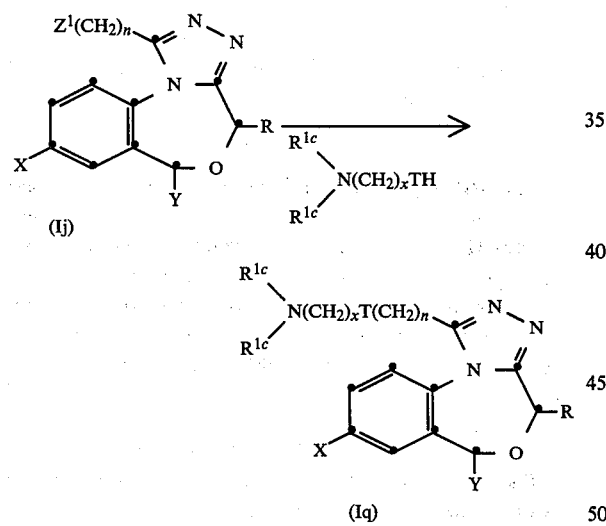

(Ij)

(Iq)

(wherein
R, $R^{1c}$, n, X, Y, and $Z^1$ are the same as mentioned above;
x is an integer of 1 to 5; and
T is oxa or thia)

The compounds of the formula (Iq) are prepared by reacting the compounds (Ij) with N,N-dialkylaminoalkanols of the formula

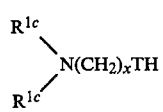

in the presence of a base. Representatives of the bases are sodium hydride and sodium amide. The reaction is carried out in an inert solvent at a temperature of $-10°$ C. to room temperature. Representatives of the inert solvents are dimethylformamide, dioxane, tetrahydrofuran, and the like.

(4) In cases that

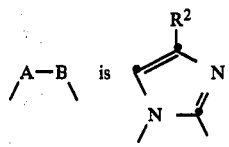

A—B is

Reaction Scheme L

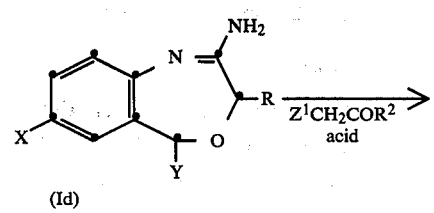

(Id)

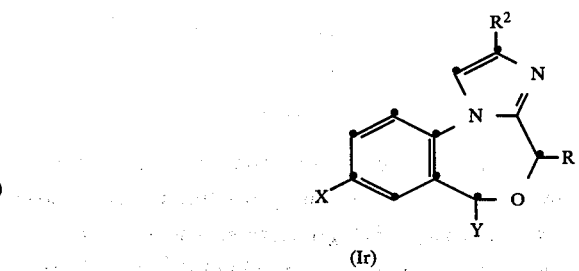

(Ir)

(wherein R, $R^2$, X, Y and $Z^1$ are the same as mentioned above)

The compounds of the formula (Ir) are prepared by reacting the compounds (Id) with an alkanoylmethyl halide of the formula $Z^1CH_2COR^2$ in the presence of an acid. The reaction may be effected in the same manner as in the 1st step of Reaction Scheme F.

(5) In cases that

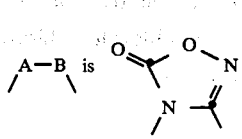

A—B is

Reaction Scheme M

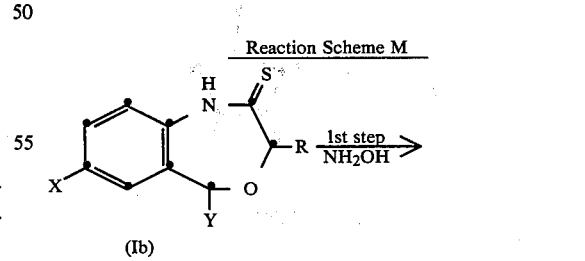

(Ib)

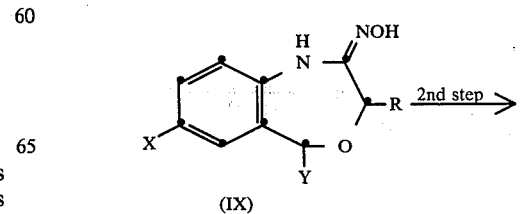

(IX)

-continued
Reaction Scheme M

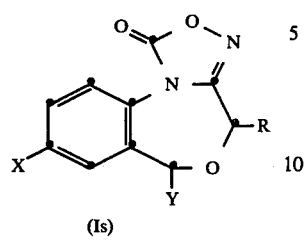
(Is)

(wherein X, Y, and R are the same as mentioned above)

(First step)

The first step, the formation of amidoximes (IX), is carried out by reacting the compounds (Ib) with hydroxylamine. The reaction is effected in an inert solvent under heating around the boiling point of the solvent. Representatives of the inert solvents are methanol, ethanol, ethyl glycol, and the like.

(Second step)

The second step, the formation of oxadiazolo compounds (Is), is carried out by reacting the compounds (IX) with an alkyl halogenocarbonate in the presence of a base. Representatives of the alkyl halogenocarbonates are methyl chlorocarbonate, ethyl chlorocarbonate, butyl chlorocarbonate, and the like. Representatives of the bases are triethylamine, tributylamine, dimethylaniline, pyridine, and the other appropriate tertiary amine. The reaction is effected in an inert solvent at room temperature or under heating around the boiling point of the solvent. Representatives of the inert solvents are ethanol, methylene chloride, chloroform, dimethylformamide, and the like.

(6) In cases that

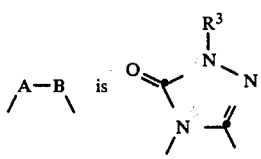

Reaction Scheme N

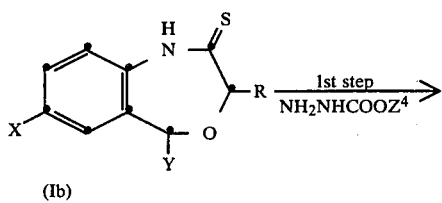
(Ib)

-continued

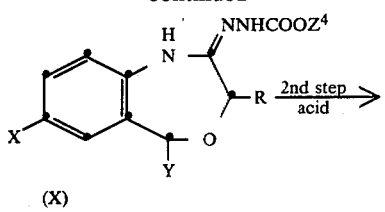
(X)

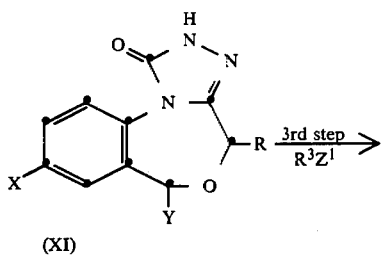
(XI)

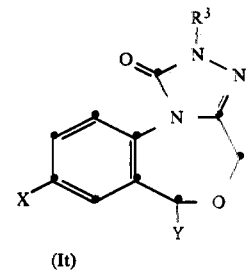
(It)

(wherein R, $R^3$, X, Y, and $Z^1$ are the same as mentioned above; and $Z^4$ is $C_1$ to $C_5$ alkyl)

(First step)

The first step, the formation of carbalkoxyhydrazono compounds (X), is carried out by reacting the compounds (Ib) with an alkyl carbazate (e.g. ethyl carbazate). The reaction is effected in an inert solvent at room temperature or under heating around the boiling point of the solvent. Representatives of the inert solvents are methanol, ethanol, chloroform, dimethylformamide, and the like.

(Second step)

The second step, the cyclization of the compounds (X) to compounds of the formula (XI), is carried out by heating the compounds (X) in the presence of an acid, preferably acetic acid at the refluxing temperature under heating.

(Third step)

The third step, the alkylation of the compounds (XI) to compounds (It), is carried out by reacting the compounds (XI) with an alkyl halide or a dialkylaminoalkyl halide in the presence of a base. The reaction is carried out in the same manner as in the 2nd step of Reaction Scheme E.

V. Effects

The following Table 1 shows results of antipentylenetetrazole test indicating anticonvulsive activities and acute toxicity.

TABLE 1

Structure: benzene ring with X substituent, A—B group, and CH(Y)—O—R side chain.

| Compound No. | X | Y | A—B | R | ED₅₀ mg/kg* in mouse | LD₅₀ mg/kg** in mouse |
|---|---|---|---|---|---|---|
| 1 | Cl | 2-Cl-phenyl | 4-methyl-3-methyl-1,2,4-triazol-5-yl | H | 1.25 | >1000 |
| 2 | " | " | 5-morpholino-4-methyl-1,2,4-triazol-3-yl | " | 4.26 | " |
| 3 | " | " | 5-(CH₃OCH₂)-4-methyl-1,2,4-triazol-3-yl | " | 2.38 | " |
| 4 | " | " | 5-(CH₃COOCH₂)-4-methyl-1,2,4-triazol-3-yl | " | 1.20 | " |
| 5 | " | " | 5-(morpholinomethyl)-4-methyl-1,2,4-triazol-3-yl | " | 3.81 | " |
| 6 | " | " | 5-(HOCH₂)-4-methyl-1,2,4-triazol-3-yl | " | 3.25 | " |
| 7 | " | " | 5-(C₂H₅OCH₂)-4-methyl-1,2,4-triazol-3-yl | " | 2.13 | " |
| 8 | " | " | 5-((CH₃)₂NCH₂)-4-methyl-1,2,4-triazol-3-yl | " | 1.02 | " |
| 9 | " | " | 5-(pyrrolidinomethyl)-4-methyl-1,2,4-triazol-3-yl | " | 4.63 | " |

TABLE 1-continued

General structure: benzene ring with X at 5-position, A—B at 2-position, and Y-O-CH(R)- forming another ring.

| Compound No. | X | Y | A—B | R | ED$_{50}$ mg/kg* in mouse | LD$_{50}$ mg/kg** in mouse |
|---|---|---|---|---|---|---|
| 10 | " | " | (CH$_3$)$_2$CHOCH$_2$-C(=N-N(CH$_3$)-N=) (triazole) | " | 2.42 | " |
| 11 | " | " | CH$_3$(CH$_2$)$_2$OCH$_2$-triazole | " | 3.09 | " |
| 12 | " | " | O=C(triazole with N-CH$_3$) | " | 3.46 | " |
| 13 | " | " | CH$_3$-triazole | CH$_3$ | 1.19 | " |
| 14 | " | " | CH$_3$COO(CH$_2$)$_2$-triazole | " | 1.67 | " |
| 15 | " | phenyl-CF$_3$ (2-CF$_3$-phenyl at X) | CH$_3$-triazole | H | 1.41 | " |
| 16 | Medazepam | | | | 4.76 | " |
| 17 | Diazepam | | | | 1.20 | " |

*Antipentylenetetrazole activity (ED$_{50}$)
**Acute toxicity (LD$_{50}$)

In determination of the antipentylenetetrazole activity, four test lots consisting of 4×10 DS male mice were employed. Within 15 minutes after single subcutaneous injection of 125 mg/kg (body weight of mouse) of pentylenetetrazole (a kind of convulsion reagent given as an aqueous solution), the mice were attacked by tonic convulsion which killed them. Test compound was orally administered 60 minutes before said s.c. injection. Observation was made for two hours postinjection of pentylenetetrazole. Anticonvulsant activity was determined in mortality percentage between 100% (all the mice dead) and 0% (all the mice alive). Test results are shown by preventive ED$_{50}$ value (Effective Doses in mg/kg, a theoretical level of 50% alive and 50% dead)[-Goodman, et al.: J. Pharmacol., 108, 168 (1953)].

Test compounds were orally administered to DS infant male mice with four toxic doses. For each dose 10 mice were used, their body weights ranging from 20 to 23 grams. Test mice were observed for 72 hours after the administration of the test compounds. Mortality was calculated by the Bliss method [Bliss: Ann. Appln. Biol., 23, 134–307 (1935); Quant. J. Pharmacol., 11, 192 (1938)].

Further, Compounds (I) showed excellent drug affinity to benzodiazepine receptors which was determined by a radio receptor assay method using receptors extracted from the brains of rats and $^3$H-diazepam. For example, 1-hydroxymethyl-6-(2-chlorophenyl)-8-chloro-4H,6H-(1,2,4)triazolo[4,3-a][4,1]benzoxazepine showed Ki=3.45 nM [Chem. Pharm. Bull., 28, 1374 (1980)].

Accordingly, Compounds (I) of the present invention are useful as sedatives, hypnotics, muscle relaxants, anticonvulsants, tymoleptics, autonomics, and the like.

VI. How to Use

Compounds (I) of this invention can be in a wide variety of oral or parenteral dosage forms solely or in admixture with other co-acting substances. The pharmaceutical compositions may be a mixture of 0.01 to 99% of Compounds (I) with a pharmaceutical carrier or carriers which can be a solid material or liquid material in which Compounds (I) are soluble, dispersible, or suspensible. They can be in a unit dosage form. The solid compositions can be in forms of tablets, powder, dry syrups, troches, granules, capsules, pills, suppositories, or like solid preparations. The liquid compositions can be in forms of injections, ointments, dispersions, inhalant, suspensions, solutions, emulsions, syrups, or elixirs. All of diluents (e.g. starch, sucrose, lactose, calcium carbonate, kaolin); bulking agents (e.g. lactose, starch, potassium carbonate, calcium phosphate, kaolin, bentonite, talc, sorbitol); binders (e.g. starch, acacia, gelatin, glucose, sodium arginate, tragacanth, carboxymethylcellulose, sorbitol, polyvinylpyrrolidone); disintegrators (e.g. starch, agar, carbonates, sodium laurylsulfate); lubricants (e.g. stearic acid, talc, paraffin, boric acid, silica, sodium benzoate, polyethyleneglycol, cacao oil, magnesium sulfate); emulsifying agents (e.g. lecithin, sorbitan monooleate, acacia); suspending agents (e.g. sorbitol, methylcellulose, glucose, sugar, gelatin, hydroxyethylcellulose, carboxymethylcellulose, aluminium stearate gel, hydrogenated fats); solvents (e.g. water, peanut oil, sesame oil, methyl oleate); preservatives (e.g. methyl or ethyl p-hydroxybenzoate, sorbic acid), edible coloring agents, aromatic substances, solubilizing agents, buffers, stabilizing agents, dispersing agents, wetting agents, antioxidants, and the like can be used in the conventional manners as far as they do not act adversely on Compounds (I).

Compounds (I) of this invention are conveniently used as solutions for intravenous, intramuscular, or subcutaneous injections according to a conventional method. Compounds (I) can be dissolved in an aqueous or oily solvent for injection to give an injectable solution in ampoule. In order to preserve the injectable preparation for a long period of time, it is appropriate to make a vial preparation containing crystals, powder, microcrystals, or lyophilizate of Compounds (I). The vial preparation may be dissolved or suspended in the said solvents for injection immediately before use. The preparation may contain said preservatives.

Compounds (I) of this invention may be administered at a daily dose of about 1 to 40 mg to an adult human. Compounds (I) may be daily administered once or 2 to 3 times in divided portions. It is appropriate to increase or decrease the dosage according to the purpose of the application, the conditions, anamnesis, and age of the patients.

The following examples are provided to further illustrate this invention.

EXAMPLE 1-(1)

2-Oxo-5-(2-trifluoromethylphenyl)-1,2,3,5-tetrahydro[4,1]-benzoxazepine

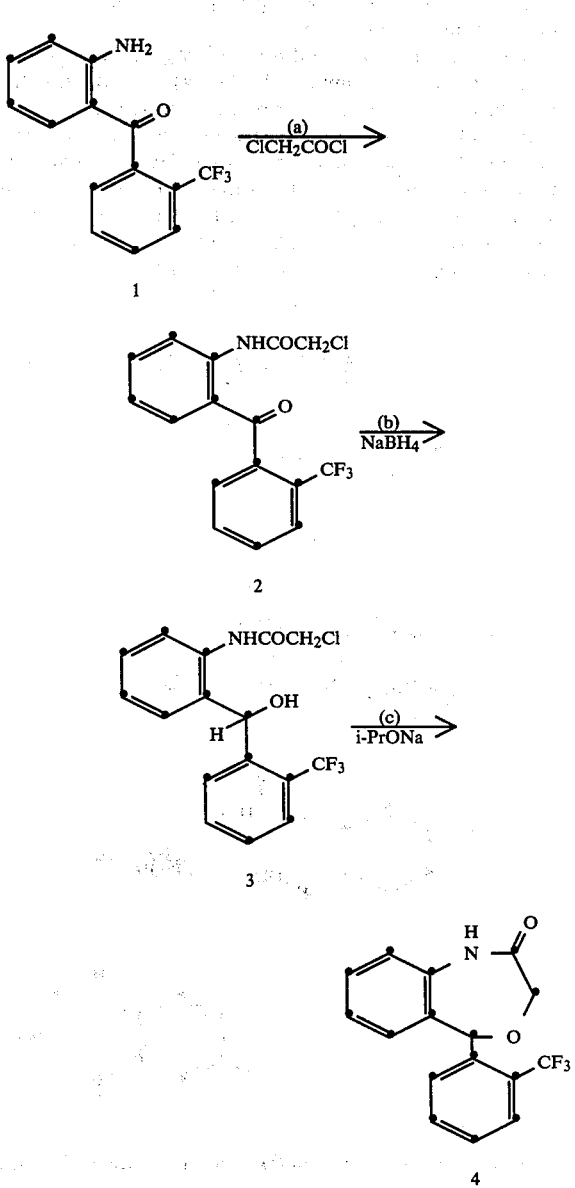

(a) To a solution of 2-amino-2'-trifluoromethylbenzophenone 1 [L. H. Sternbach et al. Helv. Chim. Acta., 45, 2226 (1962)] (8 g) in benzene (80 ml) is added chloroacetyl chloride (29 ml), and the mixture is refluxed under heating for 30 minutes. Benzene is evaporated under reduced pressure, and the residue is washed with n-hexane to give crystalline 2-(2-chloroacetyl)amino-2'-trifluoromethylbenzophenone (10.05 g), which is recrystallized from benzene-n-hexane to give the pure crystals, mp. 79°–81° C.

(b) To a solution of Compound 2 (9.8 g) in dimethylformamide (80 ml) is gradually added sodium borohydride (1.1 g) at 0° C., and the mixture is stirred at the same temperature for 2 hours, mixed with ice water, acidified with hydrochloric acid, and extracted with ethyl acetate. The organic layer is washed with water, dried over anhydrous sodium sulfate, and concentrated.

The residue is purified on column chromatography [silica gel/methylene chloride-ethyl acetate (20:3 v/v)] to give crystalline 2-(2-chloroacetyl)amino-2'-trifluoromethylbenzohydrol (4.8 g), which is recrystallized from ether-n-hexane to give pure crystals of Compound 3, mp. 116°–117° C.

(c) To a solution of sodium (500 mg) in isopropanol (100 ml) is added Compound 3 (3.6 g), and the mixture is refluxed for 30 minutes and concentrated to dryness. The residue is partitioned between ethyl acetate and dilute hydrochloric acid. The organic layer is separated, washed with water, and dried over anhydrous sodium sulfate. The solvent is evaporated under reduced pressure and the residue is washed with ether to give crystalline Compound 4, which is recrystallized from ethyl acetate to give pure crystals of Compound 4, mp. 214°–215° C.

EXAMPLES 1-(2) TO (6)

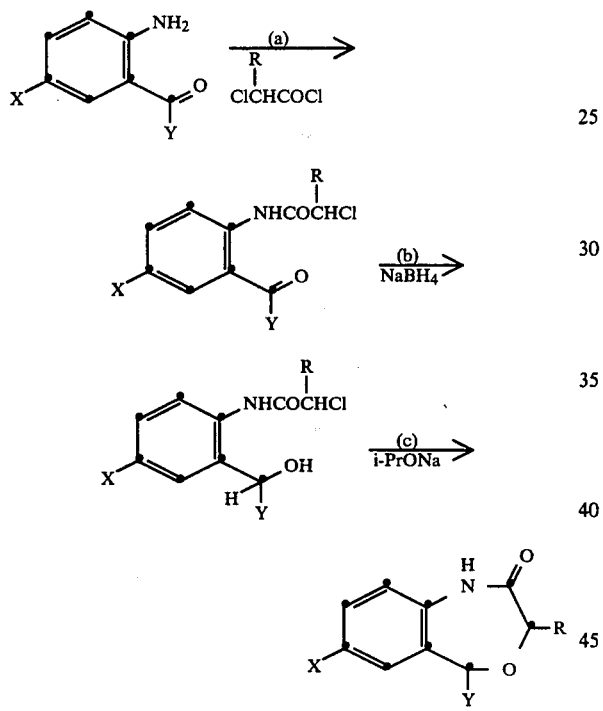

In the same manner as in Example 1-(1), the following compounds are prepared:

| Ex. No. | X | Y | R | Yield (%) |
|---|---|---|---|---|
| 1-(2) | Cl | 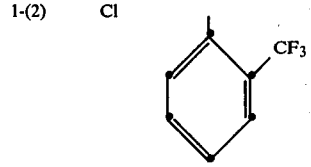 | H | 95.0 |
| 1-(3) | " | 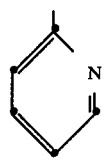 | " | 73.2 |
| 1-(4) | " | (2-Cl-phenyl) | CH₃ | 77.0 |
| 1-(5) | H | (phenyl) | H | 83.8 |
| 1-(6) | " | (4-Cl-phenyl) | " | 82.1 |

EXAMPLE 2-(1)

2-Thioxo-5-(2-trifluoromethylphenyl)-1,2,3,5-tetrahydro[4,1]-benzoxazepine

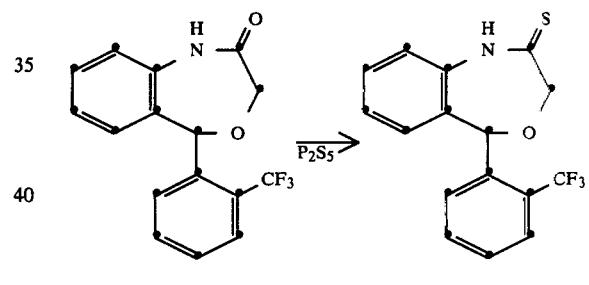

To a solution of Compound 4 prepared in Example 1-(1) (3.45 g) and sodium hydrogencarbonate (5.5 g) in tetrahydrofuran (50 ml) is added phosphorus pentasulfide (5.5 g) at 50° C., and the mixture is refluxed for 1 hour, poured into water, and extracted with ethyl acetate. The organic layer is washed with saturated brine, dried over anhydrous sodium sulfate, and concentrated under reduced pressure. The residue is purified on column chromatography (silica gel/methylene chloride). The resulting light yellow crystals are washed with n-hexane to give crystalline Compound 5 (3.1 g), which is recrystallized from ethyl acetate-n-hexane to give the title compound as pure crystals, mp. 193°–195° C.

EXAMPLES 2-(2) TO (6)

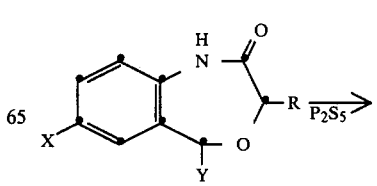

-continued

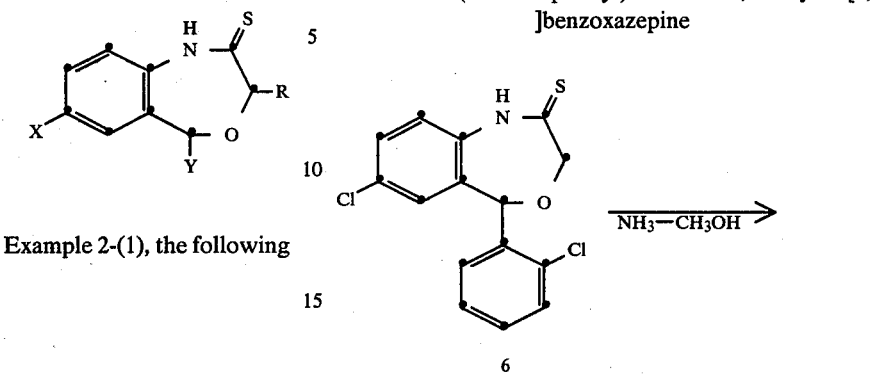

In the same manner as in Example 2-(1), the following compounds are prepared:

| Ex. No. | X | Y | R | Yield (%) |
|---|---|---|---|---|
| 2-(2) | H | 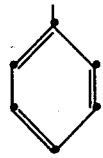 | H | 84.4 |
| 2-(3) | " | 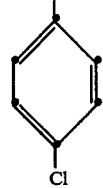 | " | 93.1 |
| 2-(4) | Cl | 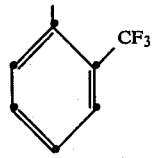 | " | 88.0 |
| 2-(5) | " | 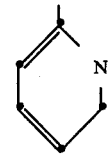 | " | 47.2 |
| 2-(6) | " | 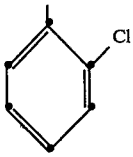 | CH₃ | 84.0 |

EXAMPLE 3

2-Amino-5-(2-chlorophenyl)-7-chloro-3,5-dihydro[4,1-]benzoxazepine

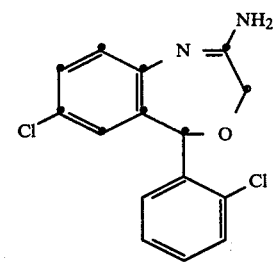

Compound 6 (U.S. Pat. No. 3,346,638)(1.95 g) is mixed with 28.6% ammonia-methanol solution (28 g), and the mixture is stirred for 3 hours. The solvent is evaporated off under reduced pressure. The residue is purified by column chromatography (silica gel/ethyl acetate) to give Compound 7 (1.6 g) in 75.5% yield, which is recrystallized from ethyl acetate.

EXAMPLE 4-(1)

6-(2-chlorophenyl)-8-chloro-4H,6H-(1,2,4)triazolo(4,3-a)[4,1]benzoxazepine

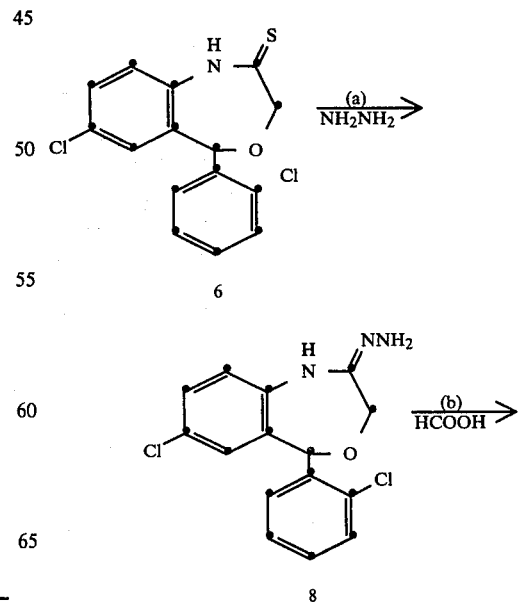

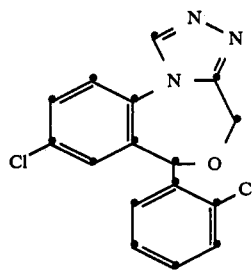

9

(a) To a solution of Compound 6 (1.62 g) in ethanol (40 ml) is added hydrazine hydrate (0.75 ml), and the mixture is stirred for 30 minutes. The solvent is evaporated under reduced pressure and the residue is extracted with chloroform. The extract is washed with water, dried, and concentrated to give Compound 8.

(b) Compound 8 is mixed with formic acid (4 ml) and refluxed under heating for 1 hour. The solvent is evaporated, and the residue is neutralized with an aqueous solution of sodium hydrogencarbonate and extracted with chloroform. The extract is washed with water, dried, and concentrated. The resulting residue is washed with diethyl ether to give Compound 9 in 96.4% yield.

EXAMPLES 4-(2) TO (3)

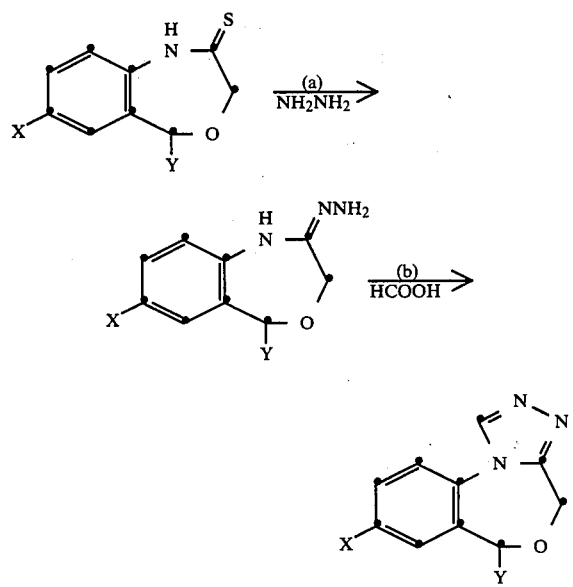

In the same manner as in Example 4-(1), the following compounds are prepared:

| Ex. No. | X | Y | solvent | Yield (%) |
|---|---|---|---|---|
| 4-(2) | Cl | 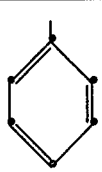 | C₂H₅OH | 87.3 |
| 4-(3) | Cl | 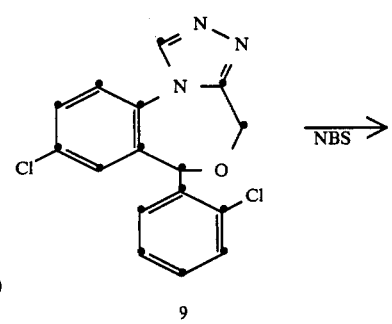 | CHCl₃ | 96.7 |

EXAMPLE 5-(1)

1-Bromo-6-(2-chlorophenyl)-8-chloro-4H,6H-(1,2,4)triazolo[4,3-a][4,1]benzoxazepine

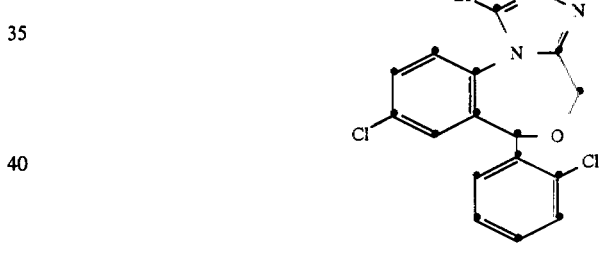

A suspension of Compound 9 prepared in Example 4-(1) (1.2 g), N-bromosuccinimide (0.675 g), and α,α'-azobis-isobutyronitrile (10 mg) in carbon tetrachloride (70 ml) is refluxed under heating for 1 hour. The insoluble materials are removed by filtration and the solvent is evaporated. The residue is treated on column chromatography (silica gel/ethyl acetate) to give the title compound (0.54 g), which is recrystallized from ethyl acetate. Yield 36.4%

EXAMPLE 5-(2)

1-Bromo-6-phenyl-8-chloro-4H,6H-(1,2,4)triazolo[4,3-a][4,1]-benzoxazepine

6-Phenyl-8-chloro-4H,6H-(1,2,4)triazolo[4,3-a][4,1]-benzoxazepine (6.85 g) is treated in the same manner as in Example 5-(1) to give the title compound (2.7 g) in 31.1% yield.

EXAMPLE 6-(1)

1-Methyl-6-(2-trifluoromethylphenyl)-4H,6H-(1,2,4)triazolo[4,3-a][4,1]benzoxazepine

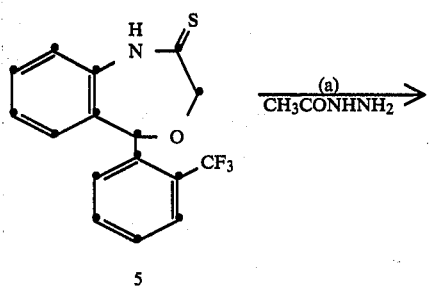

5

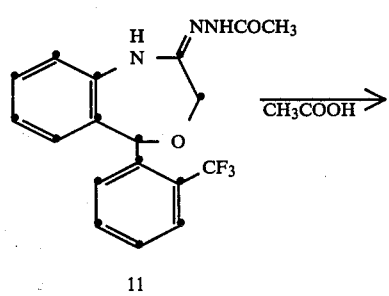

11

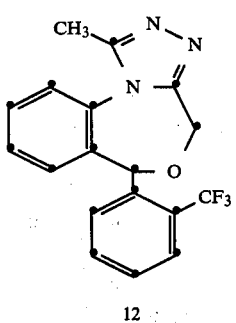

12

(a) A mixture of Compound 5 (1.3 g) and acetyl hydrazide (0.85 g) in isopropanol (30 ml) is refluxed for 1 hour and concentrated to dryness under reduced pressure to give Compound 11.

(b) Compound 11 is dissolved in acetic acid (20 ml) and the resulting solution is refluxed for 30 minutes and concentrated under reduced pressure. The residue is partitioned between ethyl acetate and aqueous sodiumm hydrogencarbonate. The organic layer is separated, dried over anhydrous sodium sulfate, and concentrated under reduced pressure. The residue is purified on column chromatography [silica gel/ethyl acetate-methanol (20:3 v/v)] to give Compound 12 (1.2 g), which is recrystallized from ethyl acetate-ether to give pure crystals of Compound 12, mp. 167°–168° C.

EXAMPLES 6-(2) TO (4)

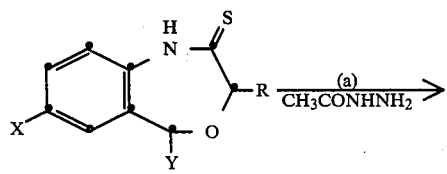

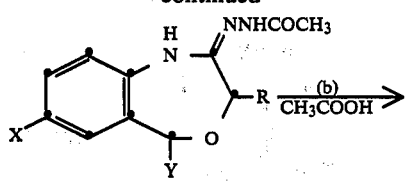

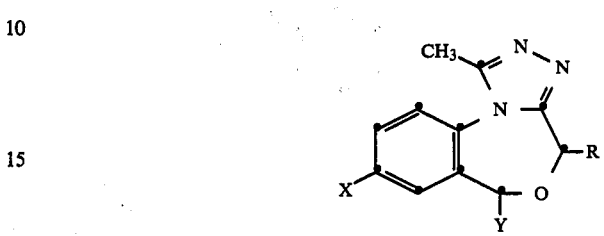

In the same manner as in Example 6-(1), the following compounds are prepared:

| Ex. No. | X | Y | R | Solvent used in step (a) | Yield (%) |
|---|---|---|---|---|---|
| 6-(2) | Cl | ![CF3-phenyl] | H | i-PrOH | 86.0 |
| 6-(3) | Cl | ![pyridyl] | H | CHCl$_3$ | 76.7 |
| 6-(4) | Cl | ![Cl-phenyl] | CH$_3$ | n-BuOH | 7[i] 24[ii] 38[iii] |

EXAMPLE 7

1-Methylthio-6-(2-chlorophenyl)-8-chloro-4H,6H-(1,2,4)triazolo[4,3-a][4,1]benzoxazepine

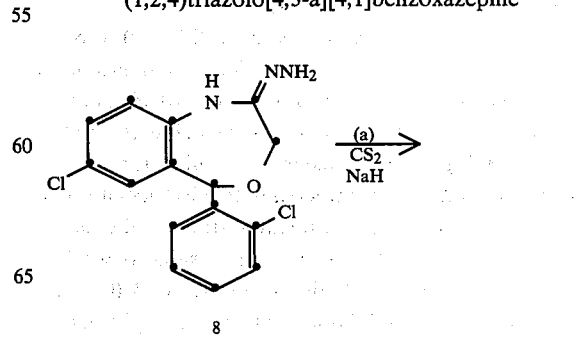

8

31

-continued

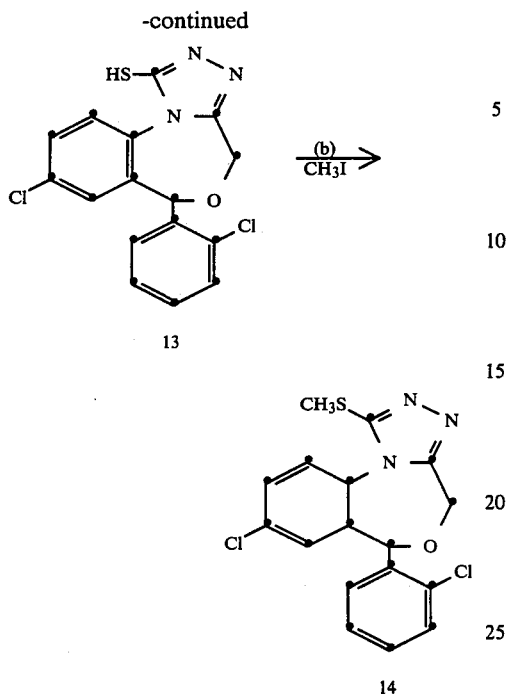

13

14

(a) A suspension of sodium hydride in mineral oil (50%)(1.3 g) is washed with n-hexane in order to remove mineral oil, mixed with tetrahydrofuran (75 ml) and imidazole (2.04 g) at −2° to 0° C. successively, and stirred for 10 minutes. Carbon disulfide (1.5 ml) is added, and the mixture is stirred for 45 minutes at the same temperature, and then 2-chloro-3-methyl-4-phenylthiazolium fluorosulfonate (4.64 g) is added. The mixture is gradually warmed up to room temperature and stirred for additional 2.5 hours. To the reaction mixture is added Compound 8 prepared in Example 4-(1)(4.83 g) at 0° to 5° C., and the mixture is gently warmed up to room temperature, stirred for 2 hours, and concentrated under reduced pressure. The residue is mixed with water, neutralized with acetic acid, and extracted with chloroform. The chloroform layer is washed with water, dried, and concentrated. The residue is treated on column chromatography (silica gel/-methylene chloride and ether). The ethereal eluate is concentrated to give Compound 13 (1.9 g), which is recrystallized from ethyl acetate to give crystals of pure Compound 13, mp. 265°–269° C.

(b) To a solution of Compound 13 (0.729 g) in N,N-dimethylformamide (6 ml) is added a suspension of sodium hydride in mineral oil (50%)(0.101 g), and the mixture is stirred for 15 minutes, mixed with methyl iodide (0.341 g), stirred under ice cooling for 1 hour, mixed with water, and extracted with ethyl acetate. The organic layer is washed with water, dried, and concentrated under reduced pressure. The residue is washed with ether to give crystalline Compound 14 (0.71 g), which is recrystallized from ethyl acetate to give Compound 14 as pure crystals, mp 176°–178° C.

32

EXAMPLE 8-(1)

1-Chloromethyl-6-(2-chlorophenyl)-8-chloro-4H,6H-(1,2,4)triazolo[4,3-a][4,1]benzoxazepine

8

15

To a solution of Compound 8 (5.85 g) prepared in Example 4-(1) in acetic acid (60 ml) is added chloroacetyl chloride (2 g), and the mixture is stirred for 1⅔ hours, mixed with sodium acetate (1.5 g), stirred for 30 minutes, refluxed under heating for 2.5 hours, and concentrated. The residue is neutralized with an aqueous solution of sodium hydrogencarbonate and extracted with chloroform. The extract is washed with water, dried, and concentrated. The residue is treated on column chromatography (silica gel/methanol) to give Compound 15 (5.1 g), which is recrystallized from ethanol. Yield 73.8%

EXAMPLE 8-(2) TO (5)

In the same manner as in Example 8-(1), the following compounds are prepared:

| Ex. No. | X | Y | R | Yield (%) |
| --- | --- | --- | --- | --- |
| 8-(2) | Cl | phenyl | H | 51.3 |
| 8-(3) | H | phenyl | H | 42.6 |
| 8-(4) | H | 4-chlorophenyl | H | 61.5 |
| 8-(5)* | Cl | 2-chlorophenyl | $CH_3$ | 56.9 + 6.3 |

*diastereomer

EXAMPLE 9-(1)

1-(4-methylpiperazino)-6-(2-chlorophenyl)-8-chloro-4H,6H-(1,2,4)triazolo[4,3-a][4,1]benzoxazepine

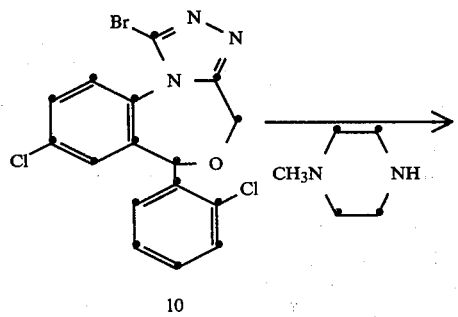

A mixture of Compound 10 (0.822 g) prepared in Example 5-(1) and N-methylpiperazine (4 ml) is stirred at 105° C. for 13 hours, mixed with water, neutralized with an aqueous solution of sodium hydrogencarbonate and extracted with chloroform. The extract is washed with water, dried, and concentrated. The residue is treated on column chromatography (silica gel/methanol) to give Compound 16 (0.52 g), which is recrystallized from ethyl acetate. Yield 86.7%

EXAMPLES 9-(2) TO (4)

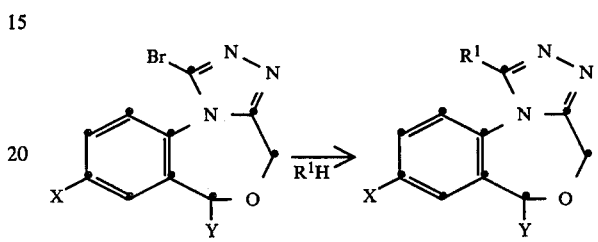

In the same manner as in Example 9-(1), the following compounds are prepared:

| Ex. No. | X | Y | $R^1$ | Yield (%) |
| --- | --- | --- | --- | --- |
| 9-(2) | Cl | phenyl | $CH_3N$-piperazine-$N-$ | 67.2 |
| 9-(3) | " | " | morpholine (O-N-) | 78.3 |
| 9-(4) | " | 2-chlorophenyl | " | 87.6 |

EXAMPLE 10

1-Mercaptomethyl-6-(2-chlorophenyl)-8-chloro-4H,6H-(1,2,4)triazolo[4,3-a][4,1]benzoxazepine

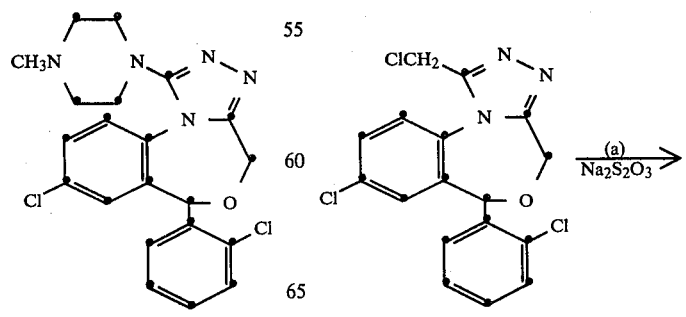

-continued

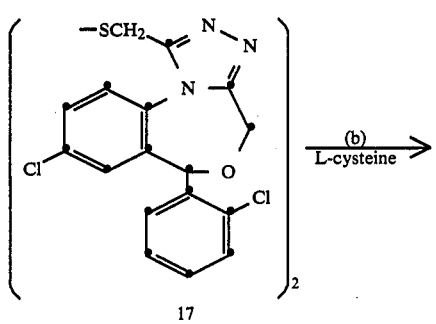

17

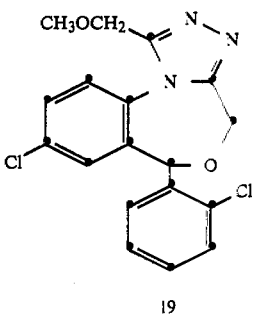

19

To a suspension of Compound 15 (0.76 g) prepared in Example 8-(1) in methanol (20 ml) is added sodium methoxide (0.119 g), and the mixture is stirred for 4 hours, allowed to stand overnight, and concentrated. The residue is extracted with chloroform and the extract is washed with water, dried, and concentrated. The residue is washed with ethyl acetate to give Compound 19 (0.5 g) in 66.5% yield.

EXAMPLES 11-(2) TO (6)

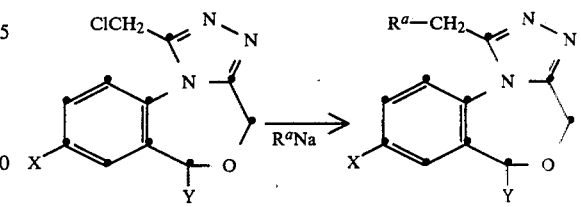

In the same manner as in Example 11-(1), the following compounds are prepared:

18

(a) A solution of Compound 15 (3.8 g) prepared in Example 8-(1) and sodium thiosulfate pentahydrate (2.98 g) in a mixture of ethanol (240 ml) and water (39 ml) is refluxed under heating for 1 hour and concentrated. The residue is mixed with water (240 ml) and sodium salt of thiol form thiamine (4.5 g), and the mixture is stirred for 4 hours and allowed to stand overnight. The resulting precipitate is collected by filtration to give Compound 17.

(b) A solution of Compound 17 (2.26 g) in a mixture of chloroform (60 ml), methanol (60 ml) and water (20 ml) is added L-cysteine (1.81 g), and the mixture is stirred for 4 hours. The precipitate is removed by filtration and the filtrate is concentrated under reduced pressure. The resulting residue is extracted with chloroform and the extract is washed with water, dried, and concentrated. The residue is washed with diethyl ether to give Compound 18 (1.7 g), which is recrystallized from ethyl acetate. Yield 90.4%

EXAMPLE 11-(1)

1-Methoxymethyl-6-(2-chlorophenyl)-8-chloro-4H,6H-(1,2,4)triazolo[4,3-a][4,1]benzoxazepine

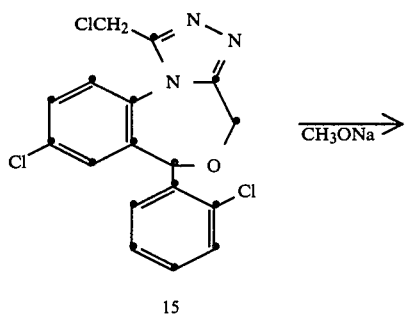

15

| Ex. No. | X | Y | $R^a$ | Yield (%) |
|---|---|---|---|---|
| 11-(2) | Cl | ⌬ | $CH_3O—$ | 93.6 |
| 11-(3) | " | ⌬Cl | $C_2H_5O—$ | 82 |
| 11-(4) | " | " | $n\text{-}C_3H_7O—$ | 76.5 |
| 11-(5) | " | " | $i\text{-}C_3H_7O—$ | 79.2 |

EXAMPLE 12

1-Acetoxymethyl-6-(2-chlorophenyl)-8-chloro-4H,6H-(1,2,4)triazolo[4,3-a][4,1]benzoxazepine

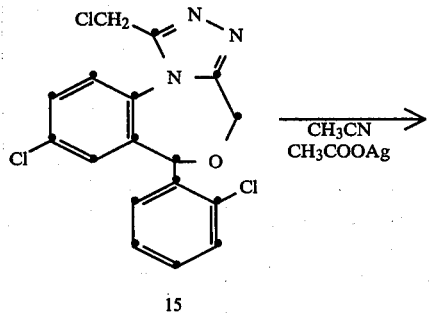

15

$\xrightarrow[\text{CH}_3\text{COOAg}]{\text{CH}_3\text{CN}}$

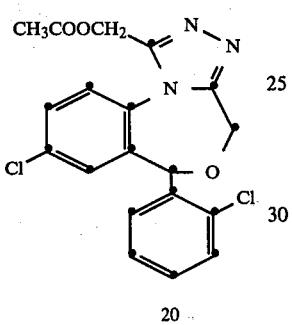

20

To a suspension of Compound 15 (0.76 g) prepared in Example 8-(1) in acetonitrile (20 ml) is added silver acetate (0.314 g), and the mixture is stirred for 4 hours, allowed to stand overnight, and concentrated. The residue is extracted with chloroform and the extract is washed with water, dried, and concentrated. The residue is washed with ethyl acetate to give Compound 20 (0.73 g) in 81.1% yield.

EXAMPLE 13

1-Hydroxymethyl-6-(2-chlorophenyl)-8-chloro-4H,6H-(1,2,4)triazolo[4,3-a][4,1]benzoxazepine

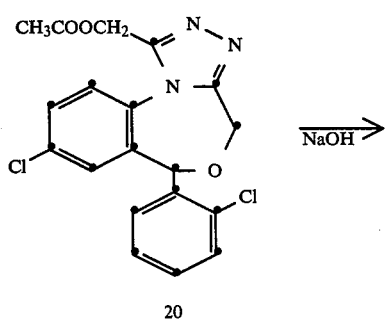

20

$\xrightarrow{\text{NaOH}}$

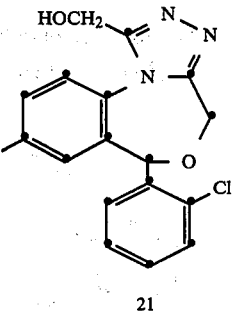

21

To a solution of Compound 20 (0.85 g) prepared in Example 12 in methanol (100 ml) is added an aqueous solution of sodium hydroxide (10%)(4 ml), and the mixture is stirred for 3 hours, acidified with 10% hydrochloric acid, and concentrated. The residue is washed with water and chloroform to give Compound 21 (0.7 g) in 92% yield.

EXAMPLE 14

1-Methylthiomethyl-6-(2-chlorophenyl)-8-chloro-4H,6H-(1,2,4)triazolo[4,3-a][4,1]benzoxazepine

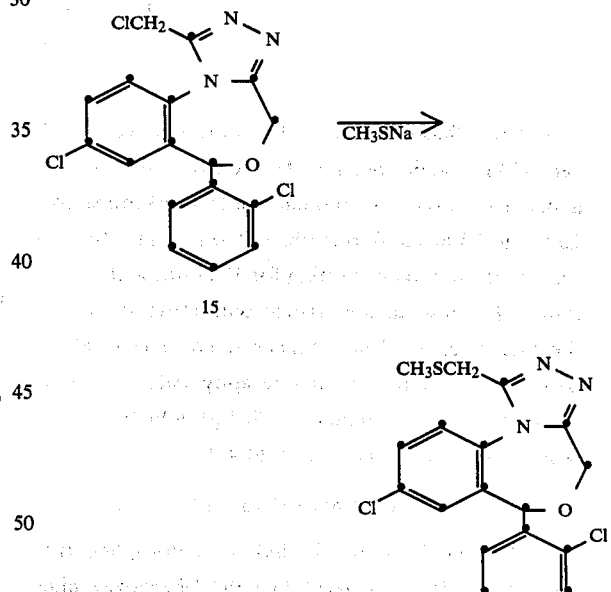

To a solution of Compound 15 (0.76 g)(prepared in Example 8-(1)) in dimethylformamide (4 ml) is added 15% sodium methylsulfide (1.12 g) under ice cooling, and the mixture is gently warmed up to room temperature, stirred for 4 hours, and then concentrated. The residue is extracted with chloroform. The extract is washed with water, dried, and concentrated. The residue is washed with diethyl ether to give Compound 22 (0.8 g), which is recrystallized from ethanol. Yield 98.3%

EXAMPLE 15

1-Benzyldithiomethyl-6-(2-chlorophenyl)-8-chloro-4H,6H-(1,2,4)triazolo[4,3-a][4,1]benzoxazepine

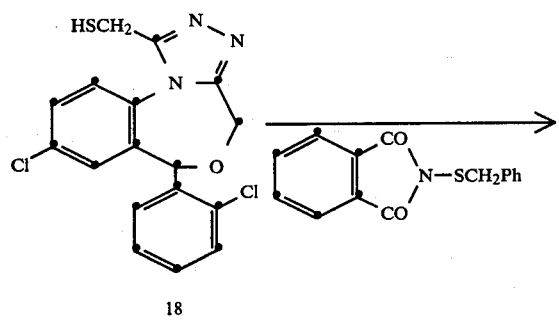

N-Benzylthiophthalimide (1.62 g) is dissolved in benzene (74 ml) under heating. To the resulting solution is added a solution of Compound 18 (1.13 g) prepared in Example 10 in dichloromethane (10 ml), and the mixture is refluxed under heating for 15 hours, and concentrated. The residue is extracted with ethyl acetate and the extract is dried and concentrated. The residue is treated on column chromatography (silica gel/ethyl acetate) to give Compound 23 (0.7 g), which is recrystallized from ethyl acetate. Yield 47%

EXAMPLE 16-(1)

1-(N,N-Dimethylamino)methyl-6-(2-chlorophenyl)-8-chloro-4H,6H(1,2,4)triazolo[4,3-a][4,1]benzoxazepine

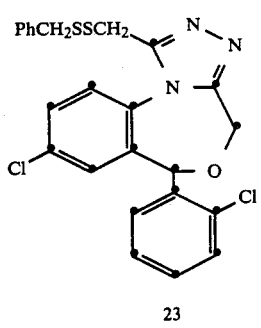

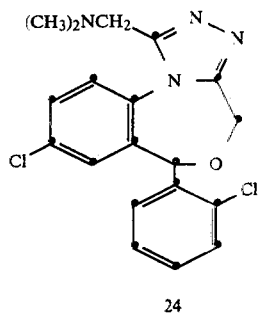

A solution of Compound 15 (0.7 g) prepared in Example 8-(1) in a mixture of ethanol (15 ml), chloroform (15 ml), and 50% dimethylamine (1.5 ml) is stirred for 2.5 hours, allowed to stand at room temperature overnight, and concentrated. The resulting residue is extracted with chloroform, and the extract is washed with water, dried, and concentrated. The residue is washed with diethyl ether to give Compound 24 (0.71 g), which is recrystallized from ethyl acetate. Yield 97.8%

EXAMPLES 16-(2) TO (7)

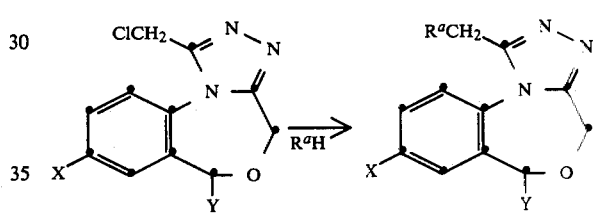

In the same manner as in Example 16-(1), the following compounds are prepared:

| Ex. No. | X | Y | $R^a$ | Yield (%) |
|---|---|---|---|---|
| 16-(2) | H | 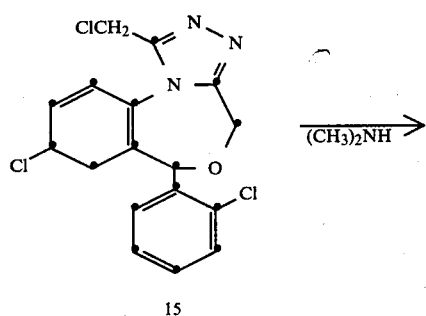 | CH₃N⟨⟩N— | 94.5 |
| 16-(3) | H | (4-Cl-phenyl) | " | 81.8 |
| 16-(4) | Cl | (phenyl) | " | 90.6 |

-continued

| Ex. No. | X | Y | $R^a$ | Yield (%) |
|---|---|---|---|---|
| 16-(5) | " | [2-chlorophenyl] | [pyrrolidin-1-yl] | 94.2 |
| 16-(6) | " | " | [morpholin-4-yl] | 96.4 |
| 16-(7) | " | " | [4-methylpiperazin-1-yl] | 98 |

EXAMPLE 17-(1)

1-[2-(N,N-Dimethylamino)ethyl]-6-(2-chlorophenyl)-8-chloro-4H,6H-(1,2,4)triazolo[4,3-a][4,1]benzoxazepine

25

↓ [(CH₃)₂N]₂CH₂

26

To a suspension of Compound 25 [U.S. patent application No. 91,814](1.73 g) in dimethylformamide (25 ml) are added bis(N,N-dimethylamino)methane (0.615 g) and acetyl chloride (0.462 ml) with ice cooling under nitrogen atmosphere, and the mixture is stirred for 2 hours, mixed with ice, neutralized with an aqueous solution of sodium hydrogencarbonate, and extracted with chloroform. The extract is washed with brine, dried, and concentrated. The residue is treated on column chromatography (silane gel/methanol) to give Compound 26 (1.55 g) in 76.7%.

EXAMPLE 17-(2)

1-[2-(N,N-Dimethylamino)ethyl]-6-phenyl-8-chloro-4H,6H-(1,2,4)triazolo[4,3-a][4,1]benzoxazepine 1-Methyl-6-phenyl-8-chloro-4H,6H-(1,2,4)triazolo[4,3-a][4,1]benzoxazepine (1.56 g) is treated in the same manner as in Example 17-(1) to give the title compound (1.3 g) in 70.5%.

EXAMPLE 18-(1)

1-(N,N-Dimethylaminopropyl)-6-(2-chlorophenyl)-8-chloro-4H,6H-(1,2,4)triazolo[4,3-a][4,1]benzoxazepine

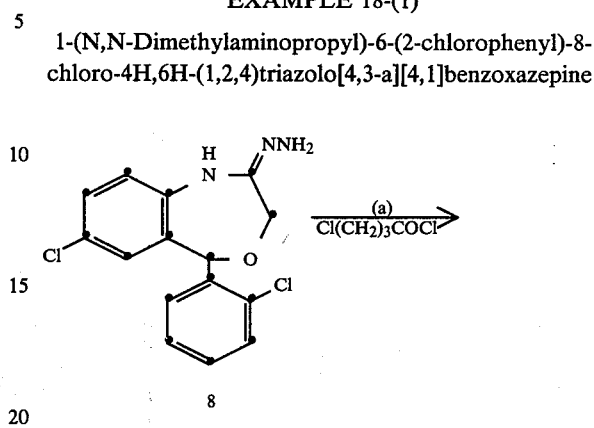

8 →(a) Cl(CH₂)₃COCl→

27 →(b) (CH₃)₂NH→

28 →(c) CH₃COOH→

29

EXAMPLE 18-(2) TO (3)

-continued

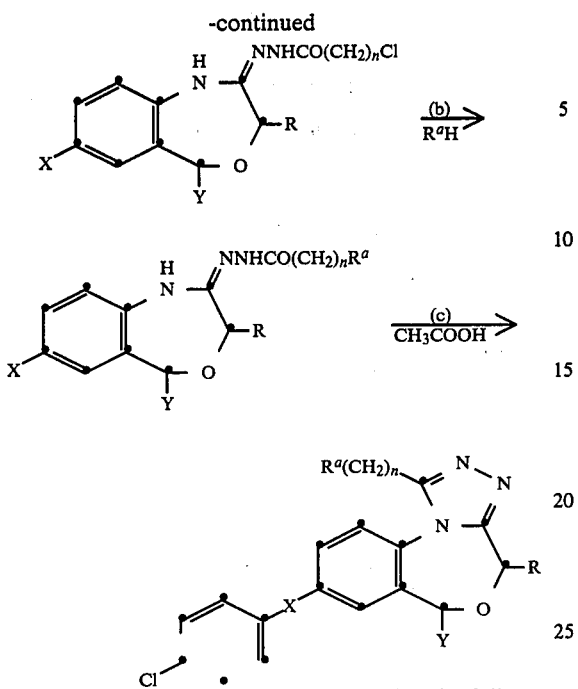

In the same manner as in Example 18-(1), the following compounds are prepared:

| Ex. No. | X | Y | $R^a$ | n | R | Yield (%) |
|---|---|---|---|---|---|---|
| 18-(2) | Cl | | CH$_3$N⟨⟩N— | 2 | H | 16.6 |
| 18-(3) | " | " | " | " | CH$_3$ | 20.4 |

(a) To a solution of Compound 8 (1.61 g) prepared in Example 4-(1) in tetrahydrofuran (20 ml) is added a solution of 4-chlorobutyryl chloride (0.7 g) in tetrahydrofuran (2.5 ml) at −5° to −2° C., and the mixture is stirred at 0° C. for 30 minutes and then at room temperature for 30 minutes.

(b) The reaction mixture containing Compound 27 is mixed with 50% aqueous dimethylamine (1.8 g) and potassium iodide (0.83 g), stirred at room temperature for 2 hours, allowed to stand for 3 days, and concentrated. The residue is extracted with chloroform. The chloroform layer is washed with water, dried, and concentrated to give Compound 28 as an oily product.

(c) Compound 28 is dissolved in acetic acid (10 ml), refluxed under heating for 3 hours, and concentrated under reduced pressure. The residue is neutralized with an aqueous solution of sodium hydrogencarbonate and extracted with chloroform. The chloroform layer is washed with water, dried, and concentrated. The residue is treated on column chromatography (silica gel/methanol) to give crystalline Compound 29 (0.55 g), which is recrystallized from ethyl acetate.

EXAMPLE 19-(1)

1-[2-(N,N-Dimethylamino)ethyloxymethyl]-6-(2-chlorophenyl)-8-chloro-4H,6H-(1,2,4)triazolo[4,3-a][4,1]benzoxazepine

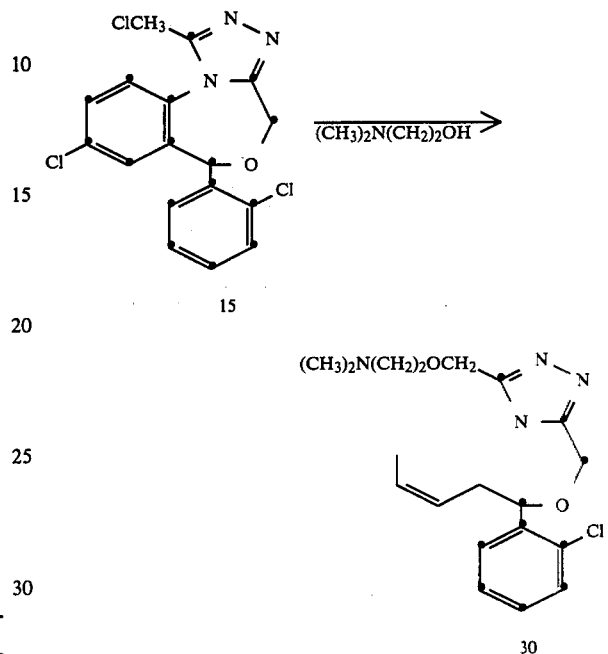

To a solution of 2-(N,N-dimethylamino)ethanol(0.29 g) in dimethylformamide (5 ml) is added a suspension of sodium hydride in mineral oil (50%)(0.132 g) at −5° C., and the mixture is stirred for 40 minutes, to which Compound 15 (0.952 g) is added, gently warmed up to room temperature, stirred for 4 hours, and concentrated. The residue is extracted with chloroform, and the extract is washed with water, dried and concentrated. The residue is treated on column chromatography (silica gel/methanol) to give Compound 39 as an oily product.

EXAMPLES 19-(2) TO (8)

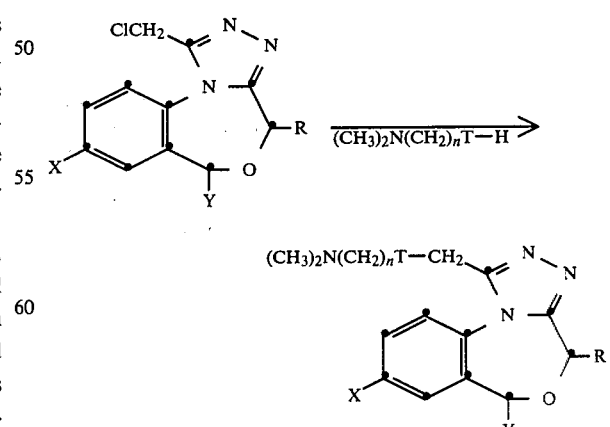

In the same manner as in Example 19-(1), the following compounds are prepared:

| Ex. No. | X | Y | n | T | R | Yield (%) |
|---|---|---|---|---|---|---|
| 19-(2) | H | (phenyl) | 2 | O | H | 79.1 |
| 19-(3) | " | (4-Cl-phenyl) | " | " | " | 60.2 |
| 19-(4) | Cl | (phenyl) | " | " | " | 66.9 |
| 19-(5) | " | (2-Cl-phenyl) | " | " | " | 56.3 |
| 19-(6) | " | " | 3 | " | " | 54.1 |
| 19-(7) | " | " | 2 | " | CH₃ | 73.9 |
| 19-(8) | " | " | " | S | H | 61.5 |

EXAMPLE 20

2-Methyl-6-(2-chlorophenyl)-8-chloro-4H,6H-imidazo[1,2-a][4,1]benzoxazepine

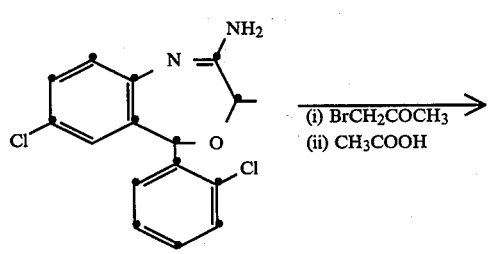

7

(i) BrCH₂COCH₃
(ii) CH₃COOH

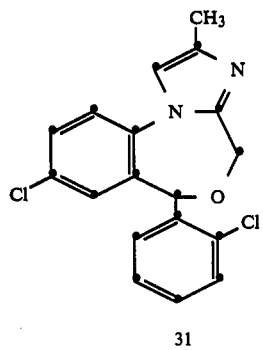

31

A solution of Compound 7 (1.1 g) prepared in Example 3 and bromoacetone (0.59 g) in ethanol (30 ml) is refluxed under heating for 3 hours. Ethanol is evaporated off under reduced pressure, and the residue is dissolved in acetic acid (10 ml), refluxed under heating for 1 hour, and concentrated under reduced pressure. The resulting residue is neutralized with an aqueous sodium hydrogencarbonate solution and then extracted with chloroform. The extract is washed with water, dried, and concentrated. The residue is treated on column chromatography to give Compound 31 (0.25 g), which is recrystallized from diethyl ether. Yield 20%

EXAMPLE 21

1-Oxo-6-(2-chlorophenyl)-8-chloro-1H,4H,6H-(1,2,4)oxadiazolo[4,3-a][4,1]benzoxazepine

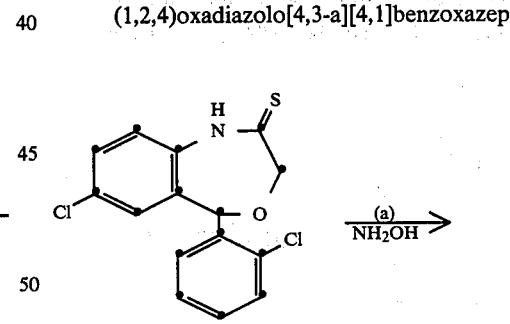

32

(a) NH₂OH →

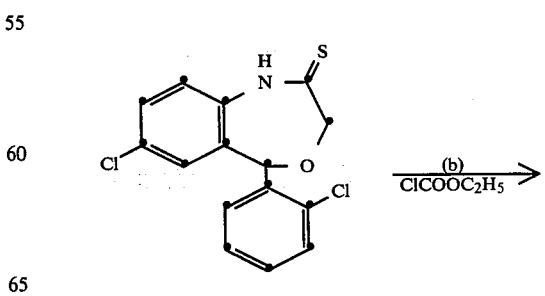

33

(b) ClCOOC₂H₅ →

-continued

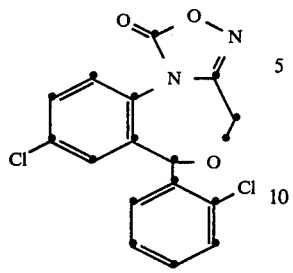

34

(a) A suspension of Compound 32 (2.3 g)(U.S. patent application No. 91,814), sodium hydrogencarbonate (0.765 g), and hydroxylamine hydrochloride (0.63 g) in methanol (35 ml) is refluxed under heating for 45 minutes and concentrated. The residue is extracted with chloroform, and the chloroform layer is washed with water, dried, and concentrated to give Compound 33 as an oily product.

(b) Compound 33 is mixed with chloroform (20 ml), triethylamine (0.708 g), and ethyl chlorocarbonate (0.76 g), and the mixture is stirred at room temperature for 20 minutes, then refluxed under heating for 3.5 hours, and washed with water. The chloroform layer is dried and concentrated to give crystalline Compound 34 (2.15 g), which is recrystallized from ethanol.

EXAMPLE 22-(1)

1-Oxo-2-methyl-6-(2-chlorophenyl)-8-chloro-1,2-dihydro-4H,6H-(1,2,4)triazolo[4,3-a][4,1]benzoxazepine

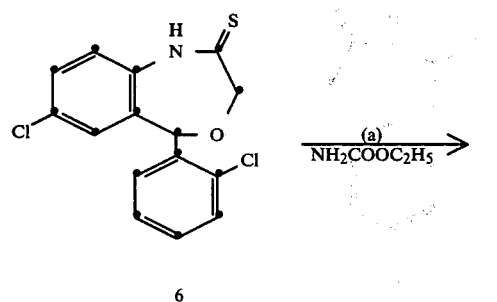

6

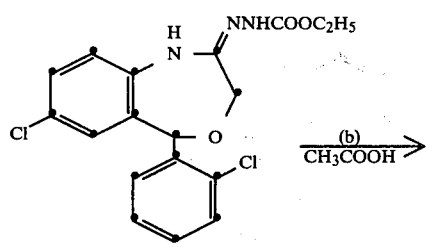

35

-continued

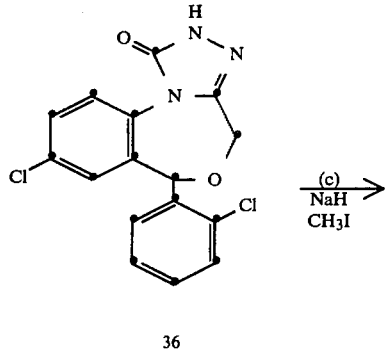

36

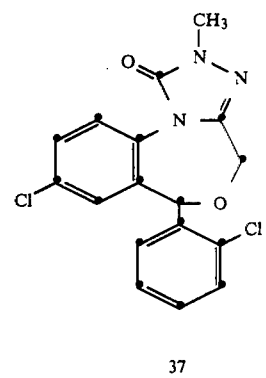

37

(a) A solution of Compound 6 (1.31 g) and ethyl carbamate (3 g) in dry ethanol (95 ml) is refluxed for 2 hours and concentrated. The residue is extracted with chloroform, and the organic layer is washed with water, dried, and concentrated under reduced pressure. The residue is washed with ether to give Compound 35 (3.7 g), which is recrystallized from ethanol. mp. 213°–215° C. (dec).

(b) A solution of Compound 35 (1.5 g) in acetic acid (10 ml) is refluxed under heating for 1⅓ hours and concentrated under reduced pressure. The residue is neutralized with an aqueous solution of sodium hydrogencarbonate and extracted with chloroform. The chloroform layer is washed with water, dried, and concentrated. The residue is treated on column chromatography (silica gel/ethyl acetate) to give Compound 36 (0.5 g), which is recrystallized from ethanol. mp. 205°–207° C.

(c) To a solution of Compound 36 (0.693 g) in dimethylformamide (4.7 ml) is added a suspension of sodium hydride in mineral oil (50%)(0.101 g), and the mixture is stirred for 30 minutes. Methyl iodide (0.34 g) is added thereto, and the reaction mixture is stirred at a temperature below 10° C. for 2 hours, mixed with water, and then extracted with ethyl acetate. The organic layer is dried and concentrated under reduced pressure. The residue is washed with ether to give crystalline Compound 37 (0.63 g), which is recrystallized from ethanol. mp. 134°–138° C.

EXAMPLE 22-(2) TO (4)
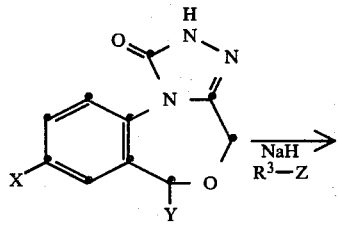
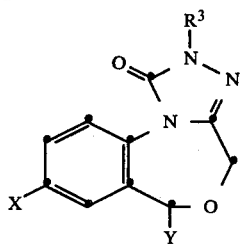
In the same manner as step (c) in Example 22-(1), the following compounds are prepared:
| Ex. No. | X | Y | R³ | Z | Yield (%) |
|---|---|---|---|---|---|
| 22-(2) | Cl | 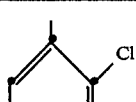 | $(CH_3)_2N(CH_2)_2-$ | Cl | 56.7 |
| 22-(3) | " | " | $(CH_3)_2N(CH_2)_3-$ | " | 43.8 |
| 22-(4) | " | " | $(C_2H_5)_2N(CH_2)_2-$ | " | 83.3 |
Physical constants of the compounds prepared in the above Examples are shown in Table 2.

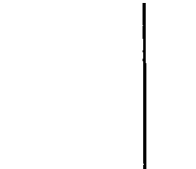

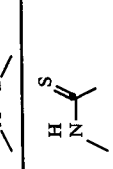

TABLE 2-continued

| | | A-B | X | m.p. | Formula / Analysis | Spectra |
|---|---|---|---|---|---|---|
| 2-(4) | | [2-CF₃-phenyl] | Cl | 143-144 | (for C₁₆H₁₁NOSF₃Cl) C, 53.71; H, 3.10; N, 3.91; S, 8.96; F, 15.93; Cl, 9.91. — C, 53.88; H, 3.31; N, 3.91; S, 9.36; F, 15.14; Cl, 10.03. | IR: ν$_{max}^{Nujol}$ 3160, 3075, 1600, 1580 cm$^{-1}$ |
| 2-(5) | | [pyridyl] | " | 188-189 | (for C₁₄H₁₁N₂SClO) C, 57.83; H, 3.81; N, 9.63; Cl, 12.19; S, 11.03. — C, 57.81; H, 3.84; N, 9.78; Cl, 12.33; S, 11.25. | 4.65s2H, 5.92s1H, 12.10br 1H (CDCl₃ + d₆DMSO) |
| 2-(6) | | [2-Cl-phenyl] | CH₃ | 209-219 | (for C₁₆H₁₁NOSCl₂) C, 56.81; H, 3.87; N, 4.14; S, 9.48; Cl, 20.96. — C, 57.01; H, 3.73; N, 4.12; S, 9.76; Cl, 20.77. | 1.53d(J = 6 Hz)3H, 4.32q (J = 6 Hz)1H, 5.98s1H, 12.2 brs1H. (CDCl₃ + d₆DMSO) |
| 3 | [C(NH₂)=N-] | " | H | 178-180(d) | (for C₁₅H₁₃N₂Cl₂O·½AcOC₂H₅) C, 57.97; H, 4.86; N, 7.95; Cl, 20.13. — C, 58.21; H, 4.46; N, 7.87; Cl, 20.45 | 4.02, 4.30ABq(J = 12 Hz)2H, 5.77s1H, 6.68br2H (CDCl₃ + d₆DMSO) |
| 4-(1) | [N-N pyrazole] | " | " | 208-210 | (for C₁₆H₁₁N₃Cl₂O) C, 57.85; H, 3.34; N, 12.65; Cl, 21.35. — C, 57.92; H, 3.33; N, 12.70; Cl, 21.22. | 4.78, 5.38ABq(J = 14 Hz)2H, 5.80s1H, 8.60s1H (CDCl₃) |

TABLE 2-continued

| No. | (left structure) | X | (ring) | m.p. (°C) | Analysis | NMR/IR |
|---|---|---|---|---|---|---|
| 4-(2) | " | | benzene | 171-173 | (for C₁₆H₁₂N₃ClO) C, 64.54; H, 4.06; N, 14.11; Cl, 11.91. — C, 64.58; H, 3.88; N, 13.99; Cl, 12.03. | 4.78, 5.13ABq(J = 14 Hz)2H, 5.60s1H, 8.38s1H (CDCl₃) |
| 4-(3) | " | | pyridine | 155-157 | (for C₁₅H₁₁N₄ClO) C, 60.31; H, 3.71; N, 18.75; Cl, 11.87. — C, 60.74; H, 3.75; N, 18.86; Cl, 12.02. | 4.87, 5.13ABq(J = 13 Hz)2H, 5.72s1H, 8.30s1H (CDCl₃) |
| 5-(1) | Br-substituted imidazole | | Cl-benzene | 188-189 | (for C₁₆H₁₀N₃Cl₂BrO) C, 46.75; H, 2.47; N, 10.22; Cl, 17.25; Br, 19.44. — C, 46.72; H, 2.45; N, 10.20; Cl, 17.01; Br, 19.17. | 4.47, 5.23ABq(J = 13 Hz)2H, 3.93s1H (CDCl₃) |
| 5-(2) | " | | benzene | 203-207 | (for C₁₆H₁₁N₃ClBrO) C, 51.02; H, 2.94; N, 11.16; Cl, 9.41; Br, 21.21. — C, 51.15; H, 3.02; N, 11.02; Cl, 9.35; Br, 21.06. | 4.68, 4.98ABq(J = 14 Hz)2H, 5.63s1H (CDCl₃) |
| 6-(1) | CH₃-substituted imidazole | H | CF₃-benzene | 167-168 | (for C₁₈H₁₄N₃OF₃) C, 62.61; H, 4.09; N, 12.17; F, 16.50. — C, 62.66; H, 4.22; N, 12.05; F, 16.48. | 2.67s3H, 4.50, 5.23ABq(J = 13 Hz)2H, 5.80s1H, 6.67-8.23 m8H.(CDCl₃) IR: ν_max^Nujol 1600, 1580 cm⁻¹. |

TABLE 2-continued

![structure: A-B ring with R, O, Y, X substituents]

| | | A—B | X | Y | R | m.p. | Analysis | NMR |
|---|---|---|---|---|---|---|---|---|
| 6-(2) | [CH3S-pyrazole-N-CH3] | " | Cl | " | | 233–234 | (for C18H13N3OF3Cl) C, 56.93; H, 3.45; N, 11.06; F, 15.01; Cl, 9.34. | C, 56.99; H, 3.31; N, 11.15; F, 14.95; Cl, 9.40. | 2.63s3H, 4.47, 5.20ABq(J = 13 Hz)2H, 5.67s1H, 6.65–8.13m7H.(CDCl3) IR: $\nu_{max}^{Nujol}$ 1600, 1580 cm$^{-1}$. |
| 6-(3) | " | " | " | " | | 184–187 | (for C16H15N4ClO) C, 61.45; H, 4.19; N, 17.91; Cl, 11.34. | C, 61.61; H, 4.12; N, 17.77; Cl, 11.36. | 2.43s3H, 4.82s2H, 5.67s1H (CDCl3) |
| 6-(4) | " | [Cl-pyridine ring] | CH3 | (i)174–176 | | | (for C18H15N3OCl2) C, 60.01; H, 4.20; N, 11.66; Cl, 19.68. | C, 60.23; H, 4.05; N, 11.68; Cl, 19.70. | 1.48d(J = 7 Hz)3H, 5.40q(J = 7 Hz)1H, 2.53s3H, 5.90s1H (CDCl3) |
| | | | | (ii)246–248 | | | (for C18H15N3OCl2) C, 60.01; H, 4.20; N, 11.66; Cl, 19.68. | C, 60.04; H, 4.00; N, 11.69; Cl, 19.80. | 1.88d(J = 7 Hz)3H, 4.65q(J = 7 Hz)1H, 2.67s3H, 5.60s1H. (CDCl3) |
| 7 | [CH3S-pyrazole-N-CH3] | " | H | " | | 176–178 | (for C17H13N3Cl2SO) C, 53.98; H, 3.46; N, 11.11; Cl, 18.74; S, 8.48. | C, 53.97; H, 3.40; N, 11.15; Cl, 18.95; S, 8.69. | 2.78s(3H), 4.48, 5.23ABq(J = 13 Hz)2H, 5.70s1H. (CDCl3) |
| 8-(1) | [ClCH2-pyrazole-N-CH3] | " | " | " | | 155–157 | (for C17H12N3Cl3O) C, 53.64; H, 3.18; N, 11.04; Cl, 27.94. | C, 53.81; H, 3.14; N, 11.21; Cl, 27.73. | 4.50, 5.28ABq(J = 13 Hz)2H, 4.77, 5.07ABq(J = 13 Hz)2H, 5.57s1H (CDCl3) |
| 8-(2) | " | [benzene ring] | " | " | | 141–143 | (for C17H13N3Cl2O) C, 58.98; H, 3.78; N, 12.14; Cl, 20.48. | C, 59.12; H, 3.61; N, 12.09; Cl, 20.24. | 4.70, 5.02ABq(J = 13 Hz)2H, 4.72s2H, 5.55s1H (CDCl3) |

TABLE 2-continued

| | A—B / R, O, Y structure with X | X | m.p. | Elemental Analysis | NMR |
|---|---|---|---|---|---|
| 8-(3) | 4-Cl-phenyl | H | 153-155 | (for C₁₇H₁₄N₃ClO) C, 65.49; H, 4.53; N, 13.48; Cl, 11.37. | C, 65.73; H, 4.29; N, 13.46; Cl, 11.61. | 4.62s2H, 4.72, 4.98ABq(J = 13 Hz)2H, 5.62s1H (CDCl₃) |
| 8-(4) | " | " | 184-186(d) | (for C₁₇H₁₃N₃Cl₂O) C, 58.98; H, 3.78; N, 12.14; Cl, 20.48. | C, 59.12; H, 3.86; N, 12.40; Cl, 20.18. | 4.72, 5.00ABq(J = 13 Hz)2H, 4.75s2H, 5.60s1H (CDCl₃) |
| 8-(5) | 2-Cl-phenyl | CH₃ | 182-184 | (for C₁₈H₁₄N₃Cl₃O·½CH₃COOC₂H₅) C, 54.75; H, 4.14; N, 9.58; Cl, 24.24. (for C₁₈H₁₄N₃Cl₃O) C, 54.78; H, 3.58; N, 10.65; Cl, 26.95. | C, 55.00; H, 3.91; N, 9.75; Cl, 24.19. C, 54.68; H, 3.55; N, 10.64; Cl, 26.68. | 1.90d(J = 6 Hz)3H, 4.82, 5.11 ABq(J = 13 Hz)2H, 5.58s1H (CDCl₃) 1.53d(J = 7 Hz)3H, 5.38q(J = 7 Hz)1H, 5.87s1H (CDCl₃) |
| 9-(1) | 4-methylpiperazinyl-triazole | H | 159-161 201-203 | (for C₂₁H₂₁N₅Cl₂O) C, 58.61; H, 4.92; N, 16.27; Cl, 16.48. | C, 58.83; H, 4.78; N, 16.26; Cl, 16.50. | 2.30s3H, 4.40, 5.03ABq(J = 13 Hz)2H, 5.78s1H (CDCl₃) |
| 9-(2) | phenyl | " | 182-183 | (for C₂₁H₂₂N₅ClO) C, 63.71; H, 5.60; N, 17.69; Cl, 8.96. | C, 63.89; H, 5.56; N, 17.71; Cl, 8.92. | 2.25s3H, 4.62, 4.88ABq(J = 14 Hz)2H, 5.82s1H (CDCl₃) |

TABLE 2-continued

[Structure shown: benzene ring with A—B, R, O, Y, and X substituents]

| | | m.p. (°C) | Elemental analysis | NMR |
|---|---|---|---|---|
| 9-(3) | [morpholine-substituted triazole structure] | 178–180 | (for $C_{20}H_{19}N_4ClO_2$)<br>C, 62.75; H, 5.00;<br>N, 14.64; Cl, 9.26. | C, 62.88; H, 4.87;<br>N, 14.73; Cl, 9.29. | 4.60, 4.88ABq(J = 14 Hz)2H,<br>5.82s1H (CDCl$_3$) |
| 9-(4) | " | 227–229 | (for $C_{20}H_{18}N_4Cl_2O_2$)<br>C, 57.57; H, 4.35;<br>N, 13.43; Cl, 16.99. | C, 57.68; H, 4.21;<br>N, 13.38; Cl, 17.02. | 4.43, 5.08ABq(J = 13 Hz)2H,<br>5.80s1H (CDCl$_3$) |
| 10 | HSCH$_2$ [triazole structure] | 179–181 | (for $C_{17}H_{13}N_3Cl_2SO$)<br>C, 53.98; H, 3.46;<br>N, 11.11; Cl, 18.74;<br>S, 8.48. | C, 54.06; H, 3.58;<br>N, 10.98; Cl, 18.58;<br>S, 8.30. | 4.47, 5.20ABq(J = 13 Hz)2H,<br>5.62s1H (CDCl$_3$) |
| 11-(1) | CH$_3$OCH$_2$ [triazole structure] | 199–202 | (for $C_{18}H_{15}N_3Cl_2O_2$)<br>C, 57.46; H, 4.02;<br>N, 11.17; Cl, 18.65. | C, 57.46; H, 3.83;<br>N, 11.16; Cl, 19.11. | 3.45s3H, 4.48, 5.25ABq(J = 13 Hz)2H, 4.57, 4.83ABq(J = 12 Hz)2H, 5.58s1H (CDCl$_3$) |
| 11-(2) | " | 173–175 | (for $C_{18}H_{16}N_3ClO_2$)<br>C, 63.25; H, 4.72;<br>N, 12.29; Cl, 10.37. | C, 60.06; H, 4.49;<br>N, 12.19; Cl, 10.60. | 3.40s3H, 4.48s2H, 4.67, 5.00 ABq(J = 13 Hz)2H, 5.55s1H (CDCl$_3$) |

TABLE 2-continued

| | A—B group | X (Cl-phenyl) | m.p. | Analysis | NMR |
|---|---|---|---|---|---|
| 11-(3) | C$_2$H$_5$OCH$_2$—(triazole) | " | 175–180 | (for C$_{19}$H$_{17}$N$_3$Cl$_2$O$_2$) C, 58.47; H, 4.39; N, 10.77; Cl, 18.17. C, 58.45; H, 4.23; N, 10.69; Cl, 18.26. | 1.22t(J = 7 Hz)3H, 3.65q(J = 7 Hz)2H, 4.50, 5.25ABq(J = 13 Hz)2H, 4.57, 4.90ABq(J = 13 Hz)2H, 5.60s1H (CDCl$_3$) |
| 11-(4) | n-C$_3$H$_7$OCH$_2$—(triazole) | " | 141–143 | (for C$_{20}$H$_{19}$N$_3$Cl$_2$O$_2$) C, 59.42; H, 4.74; N, 10.39; Cl, 17.54. C, 59.51; H, 4.60; N, 10.39; Cl, 17.55. | 0.88t(J = 7 Hz)3H, 3.53t(J = 7 Hz)2H, 4.48, 5.23ABq(J = 13 Hz)2H, 4.57, 4.90ABq(J = 12 Hz)2H, 5.58s1H (CDCl$_3$) |
| 11-(5) | i-C$_3$H$_7$OCH$_2$—(triazole) | " | 134–136 | (for C$_{20}$H$_{19}$N$_3$Cl$_2$O$_2$) C, 59.42; H, 4.74; N, 10.39; Cl, 17.54. C, 59.36; H, 4.54; N, 10.37; Cl, 17.56. | 1.18d(J = 6 Hz)3H, 1.22d(J = 6 Hz)3H, 4.47, 5.23ABq(J = 13 Hz)2H, 4.55, 4.92ABq(J = 12 Hz)2H, 5.58s1H (CDCl$_3$) |
| 12 | CH$_3$COOCH$_2$—(triazole) | " | 203–204 | (for C$_{19}$H$_{15}$N$_3$Cl$_2$O$_3$) C, 56.45; H, 3.74; N, 10.39; Cl, 17.54. C, 56.44; H, 3.60; N, 10.34; Cl, 17.43. | 1.97s3H, 4.47, 5.17ABq(J = 13 Hz)2H, 5.25, 5.65ABq(J = 13 Hz)2H, 5.58s1H (CDCl$_3$) |
| 13 | HOCH$_2$—(triazole) | " | 222–224 | (for C$_{17}$H$_{13}$N$_3$Cl$_2$O$_2$) C, 56.37; H, 3.62; N, 11.60; Cl, 19.58. C, 56.52; H, 3.55; N, 11.58; Cl, 19.41. | 4.57, 5.17ABq(J = 13 Hz)2H, 4.78, 5.00ABq(J = 13 Hz)2H, 5.67s1H (d$_6$-DMSO) |
| 14 | CH$_3$SCH$_2$—(triazole) | " | 222–224 | (for C$_{18}$H$_{15}$N$_3$SCl$_2$O) C, 55.11; H, 3.85; N, 10.71; Cl, 18.07; S, 8.17. C, 55.15; H, 3.95; N, 10.70; Cl, 18.00; S, 8.30. | 2.18s3H, 3.83, 4.12ABq(J = 14 Hz)2H, 4.47, 5.23ABq(J = 13 Hz)2H, 5.57s1H (CDCl$_3$) |

TABLE 2-continued

| | A—B | X | | Elemental Analysis | NMR |
|---|---|---|---|---|---|
| 15 | PhCH₂SSCH₂ (triazole structure) | " | 172-175 | (for C₂₄H₁₉N₃S₂Cl₂O) C, 57.60; H, 3.83; N, 8.40; Cl, 14.17; S, 12.81. / C, 57.49; H, 3.69; N, 8.41; Cl, 14.33; S, 13.36. | 3.88s2H, 3.98s2H, 4.43, 5.23 ABq(J = 13 Hz)2H, 5.57s1H, 7.25s5H (CDCl₃) |
| 16-(1) | (CH₃)₂NCH₂ (triazole structure) | " | 192-194(d) | (for C₁₉H₁₈N₄Cl₂O) C, 58.62; H, 4.66; N, 14.39; Cl, 18.48. / C, 58.80; H, 4.54; N, 14.55; Cl, 18.48. | 2.32s6H, 3.67s2H, 4.47, 5.23 ABq(J = 13 Hz)2H, 5.57s1H (CDCl₃) |
| 16-(2) | morpholino-NCH₂ (triazole structure) | H | 180-182 | (for C₂₂H₂₅N₅O) C, 70.38; H, 6.71; N, 18.65. / C, 70.63; H, 6.74; N, 18.49. | 2.28s3H, 3.58s2H, 4.70, 5.02 ABq(J = 13 Hz)2H, 5.62s1H (CDCl₃) |
| 16-(3) | " | " | 168-170 | (for C₂₂H₂₄N₅ClO) C, 64.46; H, 5.90; N, 17.08; Cl, 8.65. / C, 64.28; H, 5.80; N, 17.17; Cl, 8.79. | 2.28s3H, 3.58s2H, 4.70, 4.98 ABq2H, 5.62s1H (CDCl₃) |
| 16-(4) | " | Cl | 213-125 | (for C₂₂H₂₄N₅ClO) C, 64.46; H, 5.90; N, 17.08; Cl, 8.65. / C, 64.58; H, 5.83; N, 16.90; Cl, 8.83. | 2.30s3H, 3.57s2H, 4.68, 5.00ABq(J = 13 Hz)2H, 5.57s1H (CDCl₃) |

TABLE 2-continued

| | | | | |
|---|---|---|---|---|
| 16-(5) | ![structure with NCH2 triazole] | ![chlorophenyl] | 162–164 | (for C21H20N4Cl2O) C, 60.73; H, 4.85; N, 13.49; Cl, 17.07. | (for C21H20N4Cl2O) C, 60.29; H, 4.71; N, 13.44; Cl, 17.23. | 3.88s2H, 4.45, 5.20ABq(J = 13 Hz)2H, 5.57s1H (CDCl3) |
| 16-(6) | ![morpholine triazole] | " | 190–191 | (for C21H20N4Cl2O2) C, 58.48; H, 4.67; N, 12.99; Cl, 16.44. | C, 58.45; H, 4.54; N, 12.93; Cl, 16.53. | 4.48, 5.25ABq(J = 13 Hz)2H, 5.57s1H (CDCl3) |
| 16-(7) | ![CH3N piperazine triazole] | " | 169–172 | (for C22H23N5Cl2O) C, 59.47; H, 5.22; N, 15.76; Cl, 15.96. | C, 59.30; H, 5.23; N, 15.60; Cl, 16.79. | 3.65, 3.93ABq(J = 13 Hz)2H, 4.48, 5.23ABq(J = 13 Hz)2H, 5.62s1H (CDCl3) |
| 17-(1) | (CH3)2N(CH2)2 triazole | ![phenyl] | 175–177 | (for C20H24N4ClO) C, 59.56; H, 5.00; N, 13.89; Cl, 17.58. | C, 59.78; H, 4.91; N, 14.02; Cl, 17.50. | 2.07s6H, 4.47, 5.20ABq(J = 13 Hz)2H, 5.62s1H (CDCl3) |
| 17-(2) | " | " | 147–148 | (for C20H21N4ClO) C, 65.12; H, 5.74; N, 15.19; Cl, 9.61. | C, 65.25; H, 5.62; N, 15.22; Cl, 9.88. | 2.13s6H, 4.60, 4.92ABq(J = 13 Hz)2H, 5.53s1H (CDCl3) |

TABLE 2-continued

![structure: benzene ring with A-B group, O-Y group, and X substituent with R]

| No. | (substituent column 1) | (ring) | R | m.p. | Analysis | NMR |
|---|---|---|---|---|---|---|
| 18-(1) | $(CH_3)_2N-(CH_2)_3$- with N-methylimidazole | 3-Cl-phenyl | | 147-149 | (for $C_{21}H_{22}N_4Cl_2O$) C, 60.44; H, 5.31; N, 13.42; Cl, 16.99. C, 60.46; H, 5.15; N, 13.46; Cl, 16.80. | 2.17s(6H), 4.47, 5.18ABq (J = 13 Hz)2H, 5.60s1H (CDCl$_3$) |
| 18-(2) | morpholine-N-(CH$_2$)$_2$- with N-methylimidazole | 3-Cl-phenyl | | 152-154 | (for $C_{23}H_{25}N_5Cl_2O$) C, 60.27; H, 5.50; N, 15.28; Cl, 15.47. C, 60.21; H, 5.41; N, 15.06; Cl, 15.31. | 2.28s3H, 2.48s8H, 4.48, 5.23ABq(J = 13 Hz)2H, 5.63s1H (CDCl$_3$) |
| 18-(3) | " | 3-Cl-phenyl | CH$_3$ | 177-178 | (for $C_{24}H_{27}N_5Cl_2O\cdot\frac{1}{2}HO$) C, 59.88; H, 5.86; N, 14.55; Cl, 14.73. C, 60.11; H, 5.60; N, 14.54; Cl, 14.80. | 1.85d(J = 6 Hz)3H, 2.27s3H, 2.47s8H, 4.57q(J = 6 Hz)1H, 5.53s1H (CDCl$_3$) |
| 19-(1) | $(CH_3)_2N(CH_2)_2OCH_2$- with N-methylimidazole | 3-Cl-phenyl | H | 157-159(d) (oxalate) | (for $C_{21}H_{24}N_4Cl_2O_2\cdot1.5(COOH)_2$) C, 50.72; H, 4.43; N, 9.86; Cl, 12.47. C, 50.75; H, 4.28; N, 9.95; Cl, 12.50. | 2.27s6H, 2.50t(J = 6 Hz)2H, 3.72 t(J = 6Hz)2H, 4.50, 5.27ABq(J = 13 Hz)2H, 4.65, 4.97ABq(J = 13 Hz) 2H, 5.62s1H (CDCl$_3$) |
| 19-(2) | " | phenyl | H | 136-138 | (for $C_{21}H_{24}N_4O_2$) C, 69.21; H, 6.64; N, 15.37; C, 69.38; H, 6.64; N, 15.63. | 2.23s6H, 2.48t(J = 6 Hz)2H, 3.63t(J = 6 Hz)2H, 4.58s2H, 4.67, 5.00ABq(J = 13 Hz)2H, 5.60s1H (CDCl$_3$) |

TABLE 2-continued

| | | | | | |
|---|---|---|---|---|---|
| 19-(3) | (structure with N-N ring, (CH₃)₂N(CH₂)₃OCH₂) | " | (4-Cl-phenyl) | 151-153 | (for C₂₁H₂₃N₄Cl₂O) C, 63.28; H, 5.66; N, 14.17; Cl, 9.03. (C, 63.23; H, 5.81; N, 14.05; Cl, 8.89.) | 2.25s6H, 2.50t(J = 6 Hz)2H, 3.67t(J = 6 Hz)2H, 4.65s2H, 4.70, 5.02ABq(J = 12 Hz)2H, 5.60s1H (CDCl₃) |
| 19-(4) | " | Cl | " | 142-143 | (for C₂₁H₂₃N₄ClO₂) C, 63.40; H, 5.76; N, 13.95; Cl, 9.07. (C, 63.23; H, 5.81; N, 14.05; Cl, 8.89.) | 2.23s6H, 2.50t(J = 5 Hz)2H, 3.65t(J = 5 Hz)2H, 4.60s2H, 4.68, 5.05ABq(J = 13 Hz)2H, 5.50s1H (CDCl₃) |
| 19-(5) | " | (2-Cl-phenyl) | " | 157-159(d) | (for C₂₁H₂₂N₄Cl₂O₂·1.5(COOH)₂) C, 50.75; H, 4.28; N, 9.95; Cl, 12.50. (C, 50.72; H, 4.43; N, 9.86; Cl, 12.47.) | 2.27s6H, 2.50t(J = 6 Hz)2H, 3.72t(J = 6 Hz)2H, 4.52, 5.27ABq(J = 13 Hz)2H, 4.65, 4.97ABq(J = 13 Hz)2H, 5.62s1H (CDCl₃) |
| 19-(6) | " | " | " | 131-133 | (for C₂₂H₂₄N₄Cl₂O₂) C, 58.80; H, 5.23; N, 12.37; Cl, 15.62. (C, 58.88; H, 5.43; N, 12.58; Cl, 15.92.) | 2.20s6H, 3.65t(J = 6 Hz)2H, 4.52, 5.23ABq(J = 13 Hz)2H, 4.60, 4.93ABq(J = 13 Hz)2H, 5.62s1H. (CDCl₃) |
| 19-(7) | " | " | CH₃ | 175-177 | (for C₂₂H₂₄N₄Cl₂O₂·1.5(COOH)₂) C, 51.62; H, 4.78; N, 9.53; Cl, 12.18. (C, 51.56; H, 4.67; N, 9.62; Cl, 12.17.) | 1.87d3H, 2.25s6H, 2.48t(J = 6 Hz)2H, 3.68t(J = 6 Hz)2H, 4.68q(J = 6 Hz)1H, 4.62, 4.95ABq(J = 13 Hz)2H, 5.53s1H (CDCl₃) |

TABLE 2-continued

| | A—B | X | | R,Y | m.p. (°C) | Analysis | NMR |
|---|---|---|---|---|---|---|---|
| 19-(8) | (CH₃)₂N(CH₂)₂SCH₂ 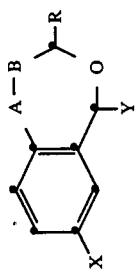 | H | | 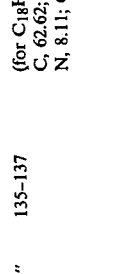 | 157–159 | (for C₂₁H₂₂N₄SCl₂O) C, 56.13; H, 4.93; N, 12.47; S, 7.13; Cl, 15.78. C, 56.16; H, 4.93; N, 12.44; S, 7.23; Cl, 15.89. | 2.27s6H, 3.75, 4.05ABq(J = 15 Hz)2H, 4.33, 5.13ABq(J = 13 Hz)2H, 5.48s1H. (CDCl₃) |
| 20 | 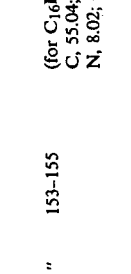 | " | | " | 135–137 | (for C₁₈H₁₄N₂Cl₂O) C, 62.62; H, 4.09; N, 8.11; Cl, 20.54. C, 62.56; H, 4.14; N, 8.06; Cl, 20.67. | 2.35s3H, 4.53, 5.05ABq(J = 13 Hz)2H, 5.78s1H, 7.10s1H (CDCl₃) |
| 21 |  | " | | " | 153–155 | (for C₁₆H₁₀N₂Cl₂O₃) C, 55.04; H, 2.89; N, 8.02; Cl, 20.31. C, 55.25; H, 2.96; N, 7.99; Cl, 20.28. | 4.57, 5.00ABq(J = 14 Hz)2H, 6.08s1H (CDCl₃) |
| 22-(1) |  | " | | " | 134–138 | (for C₁₇H₁₃N₃Cl₂O₂) C, 56.37; H, 3.62; N, 11.60; Cl, 19.58. C, 56.54; H, 3.69; N, 11.57; Cl, 19.50. | 3.57s3H, 4.55, 4.85ABq(J = 14 Hz), 5.95s1H (CDCl₃) |
| 22-(2) | (CH₂)₂N(CH₃)₂ | " | | " | 208–210(d) | (for C₂₀H₂₀N₄Cl₂O₂·(COOH)₂) C, 51.88; H, 4.35; N, 11.00; Cl, 13.92. C, 51.46; H, 4.56; N, 10.70; Cl, 13.72. | 2.33s6H, 2.77t(J = 7 Hz)2H, 4.03t(J = 7 Hz)2H, 4.45, 4.85 ABq(J = 14 Hz)2H, 5.95s1H (CDCl₃) |

TABLE 2-continued

[Structure: benzene ring with A—B substituent, X, and OCHR-Y group]

| | R | A-B | m.p. (°C) | Analysis | NMR |
|---|---|---|---|---|---|
| 22-(3) | (CH₂)₃N(CH₃)₂ | [imidazolidinone ring: N—N, with C=O and N-CH₃] | 131-134 | (for C₂₁H₂₂N₄Cl₂O₂·½H₂O·(COOH)₂) C, 51.89; H, 4.73; N, 10.52; Cl, 13.32. C, 52.13; H, 4.99; N, 10.01; Cl, 13.07. | 2.23s6H, 3.97t(J = 7 Hz)2H, 4.47, 4.85ABq(J = 13 Hz)2H, 5.93s1H (CDCl₃) |
| 22-(4) | (CH₂)₂N(C₂H₅)₂ | " | 159-163 (monooxalate) | (for C₂₂H₂₄N₄Cl₂O₂·(COOH)₂·½H₂O) C, 52.77; H, 4.98; N, 10.25; Cl, 12.98. C, 52.77; H, 4.93; N, 9.89; Cl, 12.83. | 1.03t(J = 7 Hz)6H, 2.63q(J = 7 Hz)4H, 2.90t(J = 7 Hz)2H, 4.00 t(J = 7 Hz)2H, 4.47, 4.85ABq(J = 13 Hz)2H, 5.92s1H. free; CDCl₃) |

We claim:
1. A member selected from the group consisting of a compound of the formula

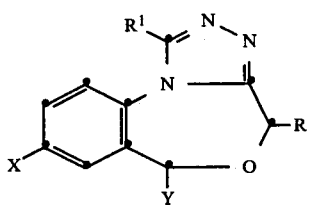

wherein
X is chlorine;
Y is 2-chlorophenyl, 2-fluorophenyl or 2-trifluoromethylphenyl;
R is hydrogen or methyl, and
$R^1$ is bromine, mercapto, mercaptomethyl, methylthio, methoxymethyl, acetoxymethyl, hydroxymethyl, chloromethyl, methylthiomethyl, benzyldithiomethyl, dimethylaminomethyl, dimethylaminoethyl, dimethylaminopropyl, dimethylaminoethoxymethyl, dimethylaminopropyloxymethyl or dimethylaminoethylthiomethyl or a pharmaceutically acceptable acid addition salt thereof.

2. A compound claimed in claim 1, namely 1-acetoxymethyl-6-(2-chlorophenyl)-8-chloro-4H,6H-(1,2,4)triazolo[4,3-a][4,1]benzoxazepine.

3. A compound claimed in claim 1, namely 1-methoxymethyl-6-(2-chlorophenyl)-8-chloro-4H,6H-(1,2,4)triazolo[4,3-a][4,1]benzoxazepine.

4. A compound claimed in claim 1, namely 1-hydroxymethyl-6-(2-chlorophenyl)-8-chloro-4H,6H-(1,2,4)triazolo[4,3-a][4,1]benzoxazepine.

5. A compound claimed in claim 1, namely 1-(N,N-dimethylamino)methyl-6-(2-chlorophenyl)-8-chloro-4H,6H-(1,2,4)-triazolo[4,3-a][4,1]benzoxazepine.

6. A pharmaceutical composition having central nervous system activity comprising an effective amount of a compound or salt thereof according to claim 1 as an effective ingredient together with a pharmaceutically acceptable carrier, diluent and/or excipient.

* * * * *